US011347000B2

(12) United States Patent
Ozcan et al.

(10) Patent No.: US 11,347,000 B2
(45) Date of Patent: May 31, 2022

(54) MICRO-PLATE READER FOR ELISA TESTING

(71) Applicant: THE REGENTS OF THE UNIVERSITY OF CALIFORNIA, Oakland, CA (US)

(72) Inventors: Aydogan Ozcan, Los Angeles, CA (US); Brandon Berg, Chatsworth, CA (US); Bingen Cortazar, Los Angeles, CA (US); Derek Tseng, Buena Park, CA (US); Steve Wei Feng, Danville, CA (US); Haydar Ozkan, Los Angeles, CA (US); Omai Garner, Culver City, CA (US); Dino Di Carlo, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 850 days.

(21) Appl. No.: 15/737,743

(22) PCT Filed: Jun. 17, 2016

(86) PCT No.: PCT/US2016/038220
§ 371 (c)(1),
(2) Date: Dec. 18, 2017

(87) PCT Pub. No.: WO2016/205736
PCT Pub. Date: Dec. 22, 2016

(65) Prior Publication Data
US 2018/0196193 A1  Jul. 12, 2018

Related U.S. Application Data

(60) Provisional application No. 62/182,312, filed on Jun. 19, 2015.

(51) Int. Cl.
G02B 6/06 (2006.01)
G06N 20/00 (2019.01)
H04N 5/225 (2006.01)
G01N 21/25 (2006.01)
(Continued)

(52) U.S. Cl.
CPC ............. G02B 6/06 (2013.01); G01N 21/253 (2013.01); G06N 20/00 (2019.01); H04N 5/225 (2013.01);
(Continued)

(58) Field of Classification Search
CPC ........ G02B 6/06; G06N 20/00; G01N 21/253; G01N 2201/0221; G01N 2201/08;
(Continued)

(56) References Cited

U.S. PATENT DOCUMENTS 5,952,202 A * 9/1999 Aoyagi ................. C07H 21/00
435/6.12
6,646,272 B2 * 11/2003 Rushbrooke ....... G01N 21/6452
250/461.1
(Continued)

FOREIGN PATENT DOCUMENTS

WO 2013/010178 A1 1/2013
WO 2015/054695 A2 4/2015

OTHER PUBLICATIONS

Roda (2011) Anal Chem 83: 3178-3185 (Year: 2011).*
(Continued)

Primary Examiner — Christopher L Chin
(74) Attorney, Agent, or Firm — Vista IP Law Group LLP

(57) ABSTRACT

A micro-plate reader for use with a portable electronic device having a camera includes an opto-mechanical attachment configured to attach/detach to the portable electronic device and includes an array of illumination sources. A slot in the opto-mechanical attachment is dimensioned to receive an optically transparent plate containing an array of wells.
(Continued)

Optical fibers are located in the opto-mechanical attachment and transmit light from each well to a reduced size header having, wherein the fiber array in the header has a cross-sectional area that is ≤10× the cross-sectional area of the wells in the plate. A lens located in the opto-mechanical attachment transmits light from the header fibers to the camera. Software executed on the portable electronic device or other computer is used to process the images to generate qualitative clinical determinations and/or quantitative index values for the separate wells.

10 Claims, 14 Drawing Sheets

(51) Int. Cl.
  *G01N 33/53* (2006.01)
  *G01N 35/00* (2006.01)

(52) U.S. Cl.
  CPC .. *B01L 2300/0829* (2013.01); *G01N 33/5304* (2013.01); *G01N 2035/00099* (2013.01); *G01N 2201/0221* (2013.01); *G01N 2201/08* (2013.01)

(58) Field of Classification Search
  CPC ..... G01N 33/5304; G01N 2035/00099; H04N 5/225; B01L 3/5085; B01L 2300/0829
  USPC ............... 422/407, 552, 553, 565, 82.05; 435/288.4; 436/809
  See application file for complete search history.

(56) References Cited

U.S. PATENT DOCUMENTS

| | | | |
|---|---|---|---|
| 2002/0060861 A1* | 5/2002 | Freber | G02B 21/34 359/799 |
| 2004/0004193 A1* | 1/2004 | Nilson | A61M 16/104 250/458.1 |
| 2010/0143200 A1* | 6/2010 | Rosselle | B01L 9/50 422/400 |
| 2011/0255745 A1* | 10/2011 | Hodder | G06T 7/0002 382/103 |
| 2012/0021525 A1* | 1/2012 | Fehr | G01N 21/6452 436/94 |
| 2012/0064564 A1* | 3/2012 | Grassl | G01N 35/028 435/29 |
| 2012/0148141 A1 | 6/2012 | Ozcan et al. | |
| 2012/0157160 A1 | 6/2012 | Ozcan et al. | |
| 2012/0218379 A1 | 8/2012 | Ozcan et al. | |
| 2012/0248292 A1 | 10/2012 | Ozcan et al. | |
| 2012/0295249 A1 | 11/2012 | Cherubini | |
| 2013/0092821 A1* | 4/2013 | Ozcan | H01L 27/14625 250/208.1 |
| 2013/0157351 A1 | 6/2013 | Ozcan et al. | |
| 2013/0203043 A1 | 8/2013 | Ozcan et al. | |
| 2014/0120563 A1* | 5/2014 | Ozcan | G01N 21/274 435/7.94 |
| 2014/0160466 A1* | 6/2014 | Muller | G01N 21/253 356/72 |
| 2014/0211204 A1 | 7/2014 | Stedtfeld et al. | |
| 2014/0323330 A1* | 10/2014 | Bergo | G01N 33/54373 506/9 |
| 2015/0104860 A1 | 4/2015 | Cunningham | |
| 2015/0111201 A1 | 4/2015 | Ozcan et al. | |
| 2015/0204773 A1 | 7/2015 | Ozcan et al. | |
| 2016/0265029 A1* | 9/2016 | Ying | G01N 21/253 |

OTHER PUBLICATIONS

Supplementary European Search Report dated Jan. 18, 2019 in European Patent Application No. 16812574, Applicant: The Regents of the University of California, (5pages).
Communication pursuant to Rules 70(2) and 70a(2) EPC dated Jan. 18, 2019 in European Patent Application No. 16812574, Applicant: The Regents of the University of California, (1page).
PCT International Search Report for PCT/US2016/038220, Applicant: The Regents of the University of California, Form PCT/ISA/210 and 220, dated Oct. 21, 2016 (5pages).
PCT Written Opinion of the International Search Authority for PCT/US2016/038220, Applicant: The Regents of the University of California, Form PCT/ISA/237, dated Oct. 21, 2016 (5pages).
Abriola, Laura et al., Digital Imaging as a Detection Method for a Fluorescent Protease Assay in 96-Well and Miniaturized Assay Plate Formats, J. Biomol. Screening 1999, 4, 121-127.
Arun, Durai et al., An Image Based Microtiter Plate Reader System for 96-well Format Fluorescence Assays, Euro. J. Biomed. Inf. 2013, 9, en58.
Gallegos, Dustin et al., Label-free biodetection using a smartphone, Lab Chip, 2013, 13, 2124-2132.
Kim, Soo Hyeon et al., Large-seal femtoliter droplet array for digital counting of single biomolecules, Lab Chip, 2012, 12, 4986-4991.
Laksanasopin, Tassaneewan et al., A smartphone dongle for diagnosis of infectious disease at the point of care, Sci. Transl. Med. 2015, 7, 273re1.
Lee, Seoho et al., A smartphone platform for the quantification of vitamin D levels, Lab Chip, 2014, 14, 1437-1442.
Long, Kenneth D. et al., Smartphone instrument for portable enzyme-linked immunosorbent assays, Biomed. Opt. Express 2014, 5, 3792-3806.
Muttan, S. et al., Image Analysis System for 96-well Plate Fluorescence Assays, 2012 Third International Conference on Computing Communication & Networking Technologies (ICCCNT) 2012, 1-6.
Oncescu, Vlad et al., Smartphone based health accessory for colorimetric detection of biomarkers in sweat and saliva, Lab Chip, 2013, 13, 3232-3238.
Preechaburana, Pakorn et al., Biosensing with cell phones, Trends Biotechnol. 2014, 32, 351-355.
Shen, Li et al., Point-of-care colorimetric detection with a smartphone, Lab Chip, 2012, 12, 4240-4243.
Soldat, Douglas J. et al., Microscale Colorimetric Analysis Using a Desktop Scanner and Automated Digital Image Analysis, J. Chem. Educ. 2009, 86, 617-620.
Sun, Steven et al., ELISA-LOC: lab-on-a-chip for enzyme-linked immunodetection, Lab Chip, 2010, 10, 2093-2100.
Wang, ShuQi et al., Integration of Cell Phone Imaging with Microchip ELISA to Detect Ovarian Cancer HE4 Biomarker in Urine at the Point-of-Care, Lab Chip 2011, 11(20), 3411-3418.
Rissin, David M. et al., Single-Molecule enzyme-linked immunosorbent assay detects serum proteins at subfemtomolar concentrations, Nat Biotechnol, Jun. 2010, 28(6), 595-599.
Breslauer, David N. et al., Mobile Phone Based Clinical Microscopy for Global Health Applications, PLoS One, www.plosone.org, Jul. 2009, vol. 4, Issue 7, e6320.
Coskun, Ahmet F. et al., Albumin testing in urine using a smartphone, DOI: 10.1039/c3lc50785h, Lab Chip, The Royal Society of Chemistry 2013.
Coskun, Ahmet F. et al., A personalized food allergen testing platform on a cellphone, Lab Chip. Feb. 21, 2013;13(4): 636-640 doi:10.1039/c21c41152k.
Erickson, David et al., Smartphone technology can be transformative to the deployment of lab-on-chip diagnosis, Lab Chip, Sep. 7, 2014; 14(17)L 3159-3164. doi:10.1039/c4lc00142g.
Lee, Myungjun et al., Field-portable reflection and transmission microscopy based on lensless holography, Sep. 1, 2011, vol. 2, No. 9, Biomedical Optics Express, 2721-2730.
McGeough, Cathy M. et al., Camera Phone-Based Quantitative Analysis of C-Reactive Protein ELISA, IEEE Transactions on Biomedical Circuits and Systems, 2012 (5pages).
Mudanyali, Onur et al., Integrated Rapid-Diagnostic-Test Reader Platform on a Cellphone, Lab Chip. Aug. 7, 2012; 12(15): 2678-2686. doi:10.1039/c21c40235a.
Ozcan, Aydogan, Mobile Phones Democratize and Cultivate Next-Generation Imaging, Diagnostics and Measurement Tools, Lab Chip. Sep. 7, 2014; 14(17): 3187-3194. doi:10.1039/c41c00010b.

(56) References Cited

OTHER PUBLICATIONS

Seo, Sungkyu et al., Lensfree holographic imaging for on-chip cytometry and diagnostics, Lab Chip, 2009, 9, 777-787.
Smith, Zachary J, et al., Cell-Phone-Based Platform for Biomedical Device Development and Education Applications, PLoS ONE, www.plosone.org, Mar. 2011, vol. 6, Issue 3, e17150.
Vashist, Sandeep Kumar et al., Cellphone-based devices for bioanalytical sciences, Anal Bioanal Chem. May 1, 2014;406(14): 3263-3277 doi:10.1007/s00216-013-7473-1.
Wei, Qingshan et al., Detection and Spatial Mapping of Mercury Contamination in Water Samples Using a Smart-Phone, ACSNano, www.acsnano.org, vol. 8, No. 2, 1121-1129, 2014.
Zhu, Hongying et al., Cost-effective and compact wide-field fluorescent imaging on a cell-phone, Lab Chip. Jan. 21, 2011; 11(2):315-322 doi:10.1039/c01c00358a.
Zhu, Hongying et al., Cost-effective and Rapid Blood Analysis on a Cell-phone, Lab Chip, Apr. 7, 2013; 13(7):1282-1288. doi:10.1039/c3lc41408f.
Zhu, Hongying et al., Optofluidic Fluorescent Imaging Cytometry on a Cell Phone, Anal Chem., Sep. 1, 2011, 83(17):6641-6647. doi:10.1021/ac201587a.
Response to the extended European search report (Rule 70a(2) EPC) dated Sep. 3, 2019 in European Patent Application No. 16812574.8, (58 pages).
Communication under Rule 71(3) EPC dated Feb. 4, 2020 inEuropean Patent Application No. 16812574.8, (7 pages).
PCT International Preliminary Report on Patentability (Chapter 1 of the Patent Cooperation Treaty) for PCT/US2016/038220, Applicant: The Regents of the University of California, Form PCT/IB/326 and 373, dated Dec. 19, 2017 (7pages).
Office Action dated Feb. 4, 2021 in U.S. Appl. No. 16/477,193, filed Jul. 11, 2019, Inventor: Aydogan Ozcan, (44 pages).
Cathy M. McGeough et al., Camera Phone-Based Quantitative Analysis of C-Reactive Protein ELISA, IEEE Transactions on Biomedical Circuits and Systems, vol. 7, No. 5, 655-659, Oct. 2013.
Office Action dated May 24, 2021 in U.S. Appl. No. 16/477,193, filed Jul. 11, 2019, Inventor: Aydogan Ozcan, (38 pages).
Pakorn Preechaburana et al., Biosensing with cell phones, Trends in Biotechnology, Jul. 2014, vol. 32, No. 7, 351-355.

* cited by examiner

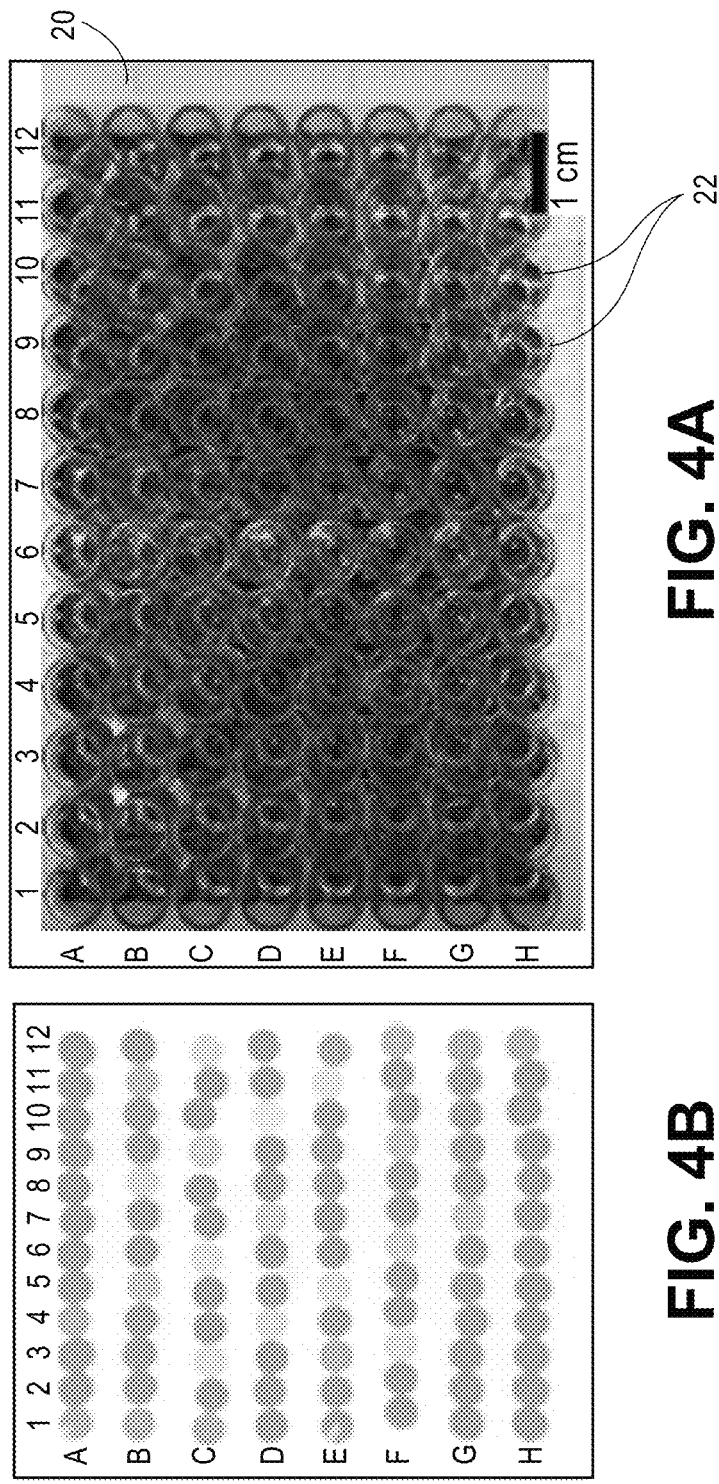

ELISA

| | 2015/11/26 7:52pm measles, mumps |
| | 2015/11/25 4:30pm HSV1, HSV2 |
| | 2015/11/24 4:44pm measles |
| | 2015/11/24 12:25pm HSV1, HSV2 |
| | 2015/11/23 1:28pm measles, mumps |

Main Menu

*University of California, Los Angeles*

ELISA
qualitative quantitiv

| | A | B | C | D | E | F | G | H |
|---|---|---|---|---|---|---|---|---|
| 1 | - | - | - | - | - | - | - | - |
| 2 | - | - | - | - | - | - | - | - |
| 3 | - | - | - | - | - | - | - | - |
| 4 | - | - | - | - | - | - | - | - |
| 5 | - | - | - | - | - | - | - | - |
| 6 | N | P | P | P | P | P | N | N |
| 7 | P | N | N | N | N | N | N | N |
| 8 | P | P | P | P | P | P | P | P |
| 9 | N | N | N | P | P | P | P | P |
| 10 | N | P | P | N | N | N | N | N |
| 11 | P | N | N | N | N | N | N | N |
| 12 | P | P | P | N | N | N | N | P |

Measles: cols 6-9, 16P, 0E, 16N
Mumps: cols 10-12, 9R, 0E, 15N
Process Time: 2014/11/26 7:52pm Main Menu

*University of California, Los Angeles*

ELISA
qualitative quantitiv

| | A | B | C | D | E | F | G | H |
|---|---|---|---|---|---|---|---|---|
| 1 | - | - | - | - | - | - | - | - |
| 2 | - | - | - | - | - | - | - | - |
| 3 | - | - | - | - | - | - | - | - |
| 4 | - | - | - | - | - | - | - | - |
| 5 | - | - | - | - | - | - | - | - |
| 6 | 0.86 | 4.88 | 5.77 | 3.20 | 3.86 | 3.65 | -0.18 | 0.26 |
| 7 | 2.27 | 0.64 | 0.74 | 0.41 | 0.56 | 0.63 | 0.61 | 1.07 |
| 8 | 2.01 | 2.37 | 5.5 | 0.97 | 7.21 | 2.93 | 3.51 | 1.52 |
| 9 | -0.31 | -0.2 | -0.07 | -0.06 | -0.1 | 4.15 | 4.08 | 2.32 |
| 10 | 0.56 | 1.76 | 3.08 | 2.02 | 2.32 | 2.32 | -0.09 | 0.13 |
| 11 | 5.07 | 3.62 | 0.38 | 0.99 | 2.01 | 0.45 | 0.49 | 0.58 |
| 12 | 4.26 | 0.89 | 2.89 | 3.51 | 2.78 | 3.92 | 2.62 | 4.48 |

Measles: cols 6-9, 16P, 0E, 16N
Mumps: cols 10-12, 9R, 0E, 15N
Process Time: 2014/11/26 7:52pm Main Menu

*University of California, Los Angeles*

FIG. 5F

Mumps (N = 135)
Cell Phone Index Value (A.U.)

Percent Difference (%)

Measles (N = 143)
Cell Phone Index Value (A.U.)

Percent Difference (%)

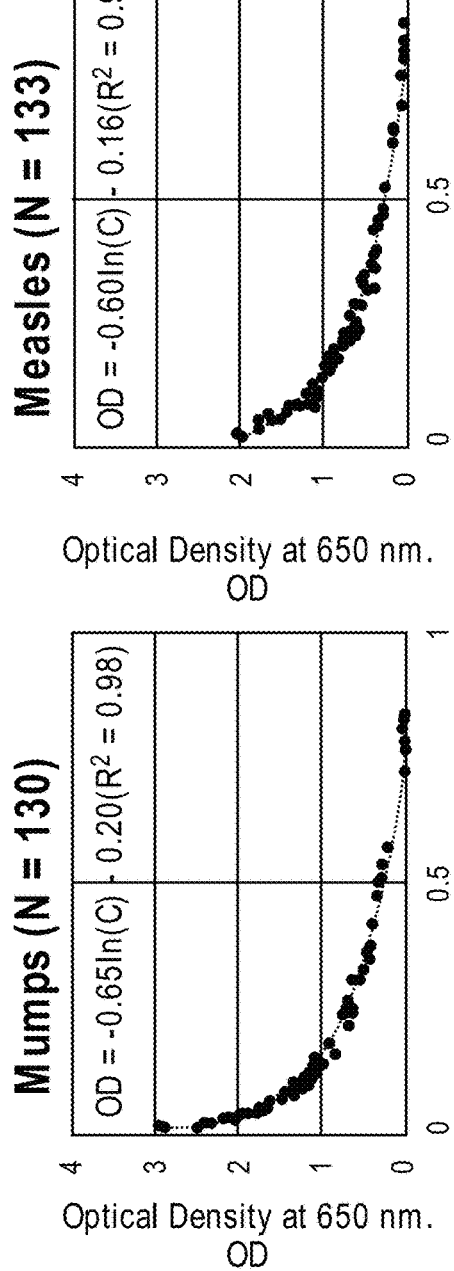
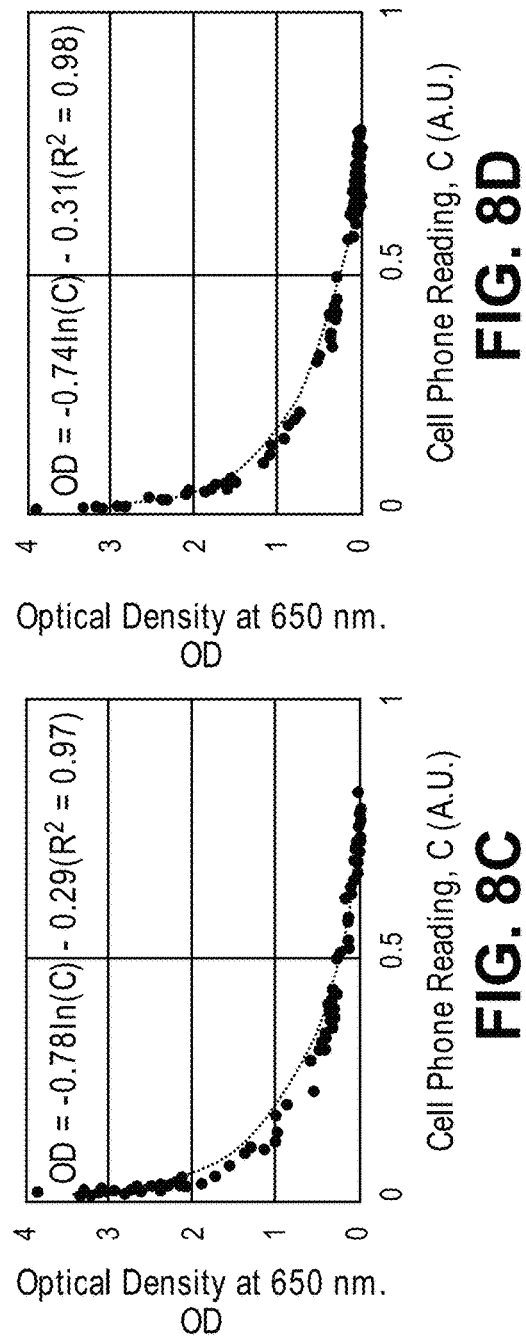
FIG. 8A
FIG. 8B
FIG. 8C
FIG. 8D

MICRO-PLATE READER FOR ELISA TESTING

RELATED APPLICATION

This Application is a U.S. National Stage filing under 35 U.S.C. § 371 of International Application No. PCT/US2016/038220, filed Jun. 17, 2016, which claims priority to U.S. Provisional Patent Application No. 62/182,312 filed on Jun. 19, 2015, which are hereby incorporated by reference. Priority is claimed pursuant to 35 U.S.C. §§ 119, 371 and any other applicable statute.

STATEMENT REGARDING FEDERALLY SPONSORED RESEARCH AND DEVELOPMENT

This invention was made with Government support under 1332275 awarded by the National Science Foundation. The Government has certain rights in the invention.

TECHNICAL FIELD

The technical field generally relates to portable diagnostic testing devices. More specifically, the technical field relates to a micro-plate reading device for spectrophotometric analysis and in particular, enzyme linked immunosorbent assay (ELISA) testing that is used in conjunction with a portable electronic device such as a mobile phone.

BACKGROUND OF THE INVENTION

Most of the commercially available technologies for point-of-care (POC) immunoassays center on lateral flow devices. Lateral flow immunoassays (LFAs) consist of prefabricated strips containing immobilized antigen and antibodies. The presence of an antibody or antigen in a specimen is recognized by binding to a region on the test strip and visualized using color-generating labels. However, this simple testing method has some inherent weaknesses compared to enzyme linked immunosorbent assay (ELISA) based tests. First, LFAs are much less sensitive than ELISA because a larger amount of antibody-antigen interactions needs to occur to create a visible signal. Second, most of the commercially available LFAs provide qualitative analyte assessment (e.g., sample is positive or negative). This limits the usefulness for vaccine effectiveness and many infectious disease diagnostics, because a semi-quantitative or quantitative assessment is clinically important. Finally, LFA tests are only designed for single test use, which makes large scale screening of populations based on LFA tests expensive and time consuming.

Immunoserological analysis is a critical component to diagnostic testing within a health care setting. Centralized laboratory testing by ELISA in a standard 96-well plate format allows for high-throughput and accurate antibody or antigen recognition for the diagnosis of many important infectious diseases, including herpes simplex virus (HSV), and vaccine effectiveness surveillance for re-emerging diseases such as measles and mumps. These laboratories require a large, integrated infrastructure including robotic systems, liquid handlers, and multi-well scanning spectrophotometers to prepare and analyze samples in batch which currently is only available in high resource capacity regions. POC immunoserological assays are available in resource limited settings, but these devices often sacrifice accuracy and can only test a limited number of patients. As the rate of infectious disease continues to increase in resource limited settings, there is a need for high-throughput and accurate POC antibody recognition platforms.

Various POC ELISA approaches have been developed recently based on, for example, microfluidic platforms or paper-based devices, among others, in order to improve accessibility in resource-limited or remote areas. Perhaps the most advanced work to date has also shown the ability to integrate a microfluidic ELISA platform with a smartphone dongle that could provide several functions including pumping and imaging of a silver precipitation readout of sandwich ELISA. See Laksanasopin et al., A smartphone dongle for diagnosis of infectious diseases at the point of care, www-.ScienceTranlationalMedicine.org, Vol. 7, Issue 273 pp. 1-9 (February 2015). This platform used a dongle containing LEDs and photodiodes for generating the optical density output signal. The dongle was connected to the mobile phone via the audio jack which functioned to power the dongle and provide for data transmission. The camera of the mobile phone was not used. This approach was applied to triplex serological analysis achieving good agreement with gold standard ELISA testing. However, using a dongle which is a non-standard disposable cartridge per patient remains relatively costly compared to standard multi-well plate based ELISA testing especially for community-wide screening and vaccine effectiveness monitoring efforts. The sensitivity of ELISA has also been tremendously improved in the past several decades with limits of detection approaching the single molecule limit by either compartmentalizing the assay into smaller volumes, a method known as the digital ELISA, or by amplifying the color change, utilizing surface plasmon enhancement effect.

Despite all the promising results obtained with these emerging approaches, 96-well plate based ELISA still remains the standard and most cost-effective tool in clinical laboratories for diagnosing diseases and monitoring the result of interventions, such as for vaccine efficacy screening. Even with an initially large capital investment, multi-well plate ELISAs are the standard format in clinical labs because sample batching and reduction in manual labor and consumables are extremely cost effective. Additionally, multi-well plate implementations of a broad range of ELISA tests are already FDA-approved, easing future regulatory burden for adaptations of these tests.

Scanning based spectrophotometry is the standard method to read colorimetric ELISA signals from 96-well plates and it requires a relatively expensive and bulky bench-top reader to individually scan each well and a reliable power grid, seriously limiting the usefulness of this method in resource-limited or remote settings. Alternatively, imaging-based detection methods which capture the entire plate in a single shot by using either a digital camera or a flatbed scanner have been developed. Optical imaging methods are favorable for rapid diagnostic purposes; however, the miniaturization of these existing imaging systems into a self-contained and robust hand-held unit remains a major challenge due to the difficulty of creating a wide field of view (FOV) image that can span the entire plate area (127×85 mm) in a compact, light-weight and cost-effective design, with minimal optical aberrations. Moreover, the ideal POC well plate reader platform would also benefit from integrating additional functionalities such as on-site image processing, wireless connectivity and a smart user-interface for immediate reporting, sharing, spatio-temporal labeling/archiving as well as visualization of diagnostic results for e.g., telemedicine and POC screening applications. Such a hand-held, cost-effective, and fully integrated plate reader system, however, has not yet been demonstrated.

Recent advances in consumer electronics and wireless communication devices have cultivated a transformation in biomedical imaging, sensing and diagnostics. By leveraging the power of semiconductor sensor chips and carry-on optics, mobile phone based devices have become a versatile microscopy and sensing platform for a wide range of applications, including blood analysis, bacteria detection, single-virus imaging, DNA imaging and sizing, chemical sensing, biomarker detection, among others. Smartphones have also been used to illuminate and image well-plate based ELISA tests. For example, Vashist et al. have disclosed a smartphone-based colorimetric reader that uses a custom made dark hood in combination with multiple portable electronic devices (e.g., mobile phone plus iPAD or iPhone). See Vashist et al., A smartphone-based colorimetric reader for bioanalytical applications using the screen-based bottom illumination provided by gadgets, Biosensors and Bioelectronics, 67, 248-255 (2015). However, the smartphone-based colorimetric reader disclosed in Vashist et al. is not hand-held and is based on a bulky imaging geometry, which exhibits optical aberrations due to its large field-of-view, also degrading its sensitivity especially for wells that are closer to the edges of the multi-well plate. It also requires multiple electronic devices (one to provide the light and another to image). In general it is also possible to use the camera of the mobile phone to capture an image of the well-plate array in ambient light conditions or using an external lamp without an additional optical design. For example, McGeough et al. have used a camera phone to image a 96 well plate to perform quantitative analysis of C-reactive protein (hs-CRP). See McGeough et al., Camera Phone-Based Quantitative Analysis of C-Reactive Protein ELISA, IEEE Transactions on Biomedical Circuits and Systems, 7, 655-659 (2013). However this simple approach has severe limitations in terms of repeatability and detection sensitivity, both of which will depend on (i) the user (e.g., in the form of uncontrolled variations in camera field-of-view and related tilts and motion artifacts), and (ii) the external lighting conditions (e.g., day vs. night). As a result of these limitations, no results from patient testing have been reported so far with this simple camera based standard multi-well plate imaging approach with ambient light.

SUMMARY

In one embodiment, a micro-plate reader for use with a portable electronic device having a camera therein includes an opto-mechanical attachment configured to attach/detach to the portable electronic device. The opto-mechanical attachment includes an array of illumination sources (e.g., light emitting diodes (LEDs)). A slot is formed in the opto-mechanical attachment and dimensioned to receive an optically transparent plate (e.g., 96-well plate) containing an array of wells therein. A base plate is located in opto-mechanical attachment and forms a bottom surface of the slot. The micro-plate reader further includes a plurality of optical fibers, wherein each optical fiber of the plurality of optical fibers terminates at a first end in the base plate to form an input array of optical fibers and terminates at a second end in a header to form an output array of optical fibers therein. Light that exits each well is captured by its own dedicated optical fiber(s). The output array of optical fibers forms an array that is much more compact and dense than the input array of optical fibers that is used to collect light from the well plate. In particular, the output array of optical fibers in the header has a cross-sectional area that is at least 10× less than a cross-sectional area of the array of wells in the optically transparent plate. A lens is disposed in the opto-mechanical attachment and interposed in an optical path formed between the array of optical fibers in the header and the camera of the portable electronic device. The lens is used to focus the image of the output array of optical fibers onto the camera of the portable electronic device.

In another embodiment, a method of using the micro-plate reader described above includes securing the opto-mechanical attachment to the portable electronic device. Samples are loaded into separate wells in the optically transparent plate and the optically transparent plate is inserted into the slot of the opto-mechanical attachment. Note that the optically transparent plate may be loaded prior to attaching the opto-mechanical attachment to the portable electronic device. The wells in the optically transparent plate are then illuminated using the array of illumination sources and one or more images of the wells with the camera of the portable electronic device are acquired. In one embodiment, the one or more images are then transmitted to a remote computer (e.g., server) or a local computer. The one or more transmitted images are then digitally processed in the remote or local computer to generate qualitative clinical determinations and/or quantitative index values for samples contained in the separate wells. The qualitative clinical determinations and/or quantitative index values for the separate wells are then transmitted or otherwise returned to the portable electronic device for display thereon.

In still another embodiment, a method of using the micro-plate reader described above includes securing the opto-mechanical attachment to the portable electronic device. Samples are loaded into separate wells in the optically transparent plate and the optically transparent plate is inserted into the slot of the opto-mechanical attachment. Again, that the optically transparent plate may be loaded prior to attaching the opto-mechanical attachment to the portable electronic device. The wells in the optically transparent plate are then illuminated using the array of illumination sources and one or more images of the wells with the camera of the portable electronic device are acquired. The one or more transmitted images are then digitally processed using the portable electronic device (using an application or other software program) to generate qualitative clinical determinations and/or quantitative index values for samples contained in the separate wells. The qualitative clinical determinations and/or quantitative index values for the separate wells can be displayed on the portable electronic device.

In still another embodiment, a method of using a micro-plate reader is disclosed that uses an opto-mechanical attachment that is attached/detached to the portable electronic device. The opto-mechanical attachment includes an input array of optical fibers that positioned beneath a well plate (e.g., 96-well plate). The input array of optical fibers may be secured in an array using columns and rows using holes or apertures formed in a base plate. The optical fibers are secured in the apertures using glue, adhesive, or the like. The optical fibers are positioned such that when an optically transparent plate (e.g., well plate) is placed on the base plate there are one or more optical fibers associated with each well. The other respective ends of the optical fibers terminate in a header that has the same array configuration but with a much higher density (e.g., higher than 10× the input side). The optical fibers at the header form an output array of optical fibers. Light that exits the wells is captured at the input array of optical fibers and transferred to the output array of optical fibers in the header. The light emitted from the columns and rows at the output array is imaged by the camera of the portable electronic device. The images are digitally processed to obtain optical density values which can then be converted to clinical values to determine whether a particular well was positive, negative, or equivocal.

In another embodiment, A method of performing ELISA testing using a portable electronic device includes securing an opto-mechanical attachment to the portable electronic device; inserting an ELISA well plate into the opto-mechanical attachment containing samples in the well plate; illuminating the ELISA well plate with an illumination source disposed in the opto-mechanical attachment; capturing illumination from individual wells of the ELISA well plate with an input array of optical fibers, wherein one or more optical fibers of the array is associated with a single well of the ELISA well plate; outputting the captured illumination from the individual wells at an output array of optical fibers, wherein the output array of optical fibers has a cross-sectional area that is at least 10× less than a cross-sectional area of the array of wells; and capturing one or more images of the illumination from the output array with a camera of the portable electronic device. In one embodiment, the images are transmitted to a remote or local computer where they are processed to generate qualitative clinical determinations and/or quantitative index values for samples contained in the separate wells. The qualitative clinical determinations and/or quantitative index values for the separate wells are then transmitted or returned to the portable electronic device for display thereon. In another embodiment, rather than being processed by a remote or local computer, the one or more transmitted images with the portable electronic device to generate qualitative clinical determinations and/or quantitative index values for samples contained in the separate wells.

BRIEF DESCRIPTION OF THE DRAWINGS

FIG. 4A illustrates a top down view of an example of an optically transparent plate in the form of a 96-well plate array that can be used with the micro-plate reader described herein.

FIG. 4B illustrates a photographic image that is obtained from camera of the portable electronic device.

FIGS. 5A-5F illustrate illustrative screen shots of the GUI presented to the user that is used to run analyze the samples contained in the wells of the optically transparent plate.

FIGS. 8A-8D illustrate calibration curves obtained for each IgG assay (mumps, measles, HSV1, HSV2), which follow a logarithmic fitting that is based on the Beer's law.

DETAILED DESCRIPTION OF THE ILLUSTRATED EMBODIMENTS

Figure 1A:
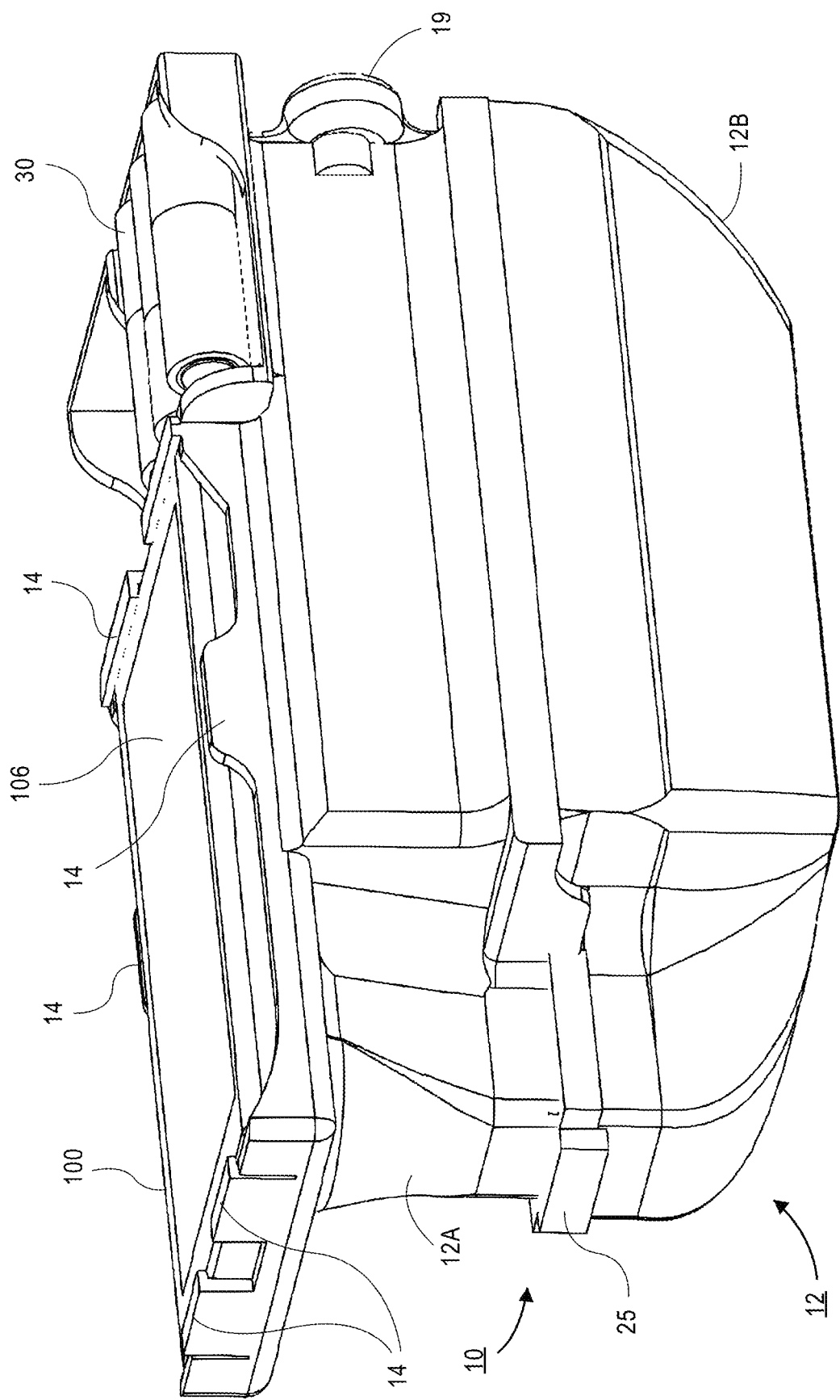
FIG. 1A illustrates a perspective view of a hand-held micro-plate reader according to one embodiment of the invention
Figure 1B:
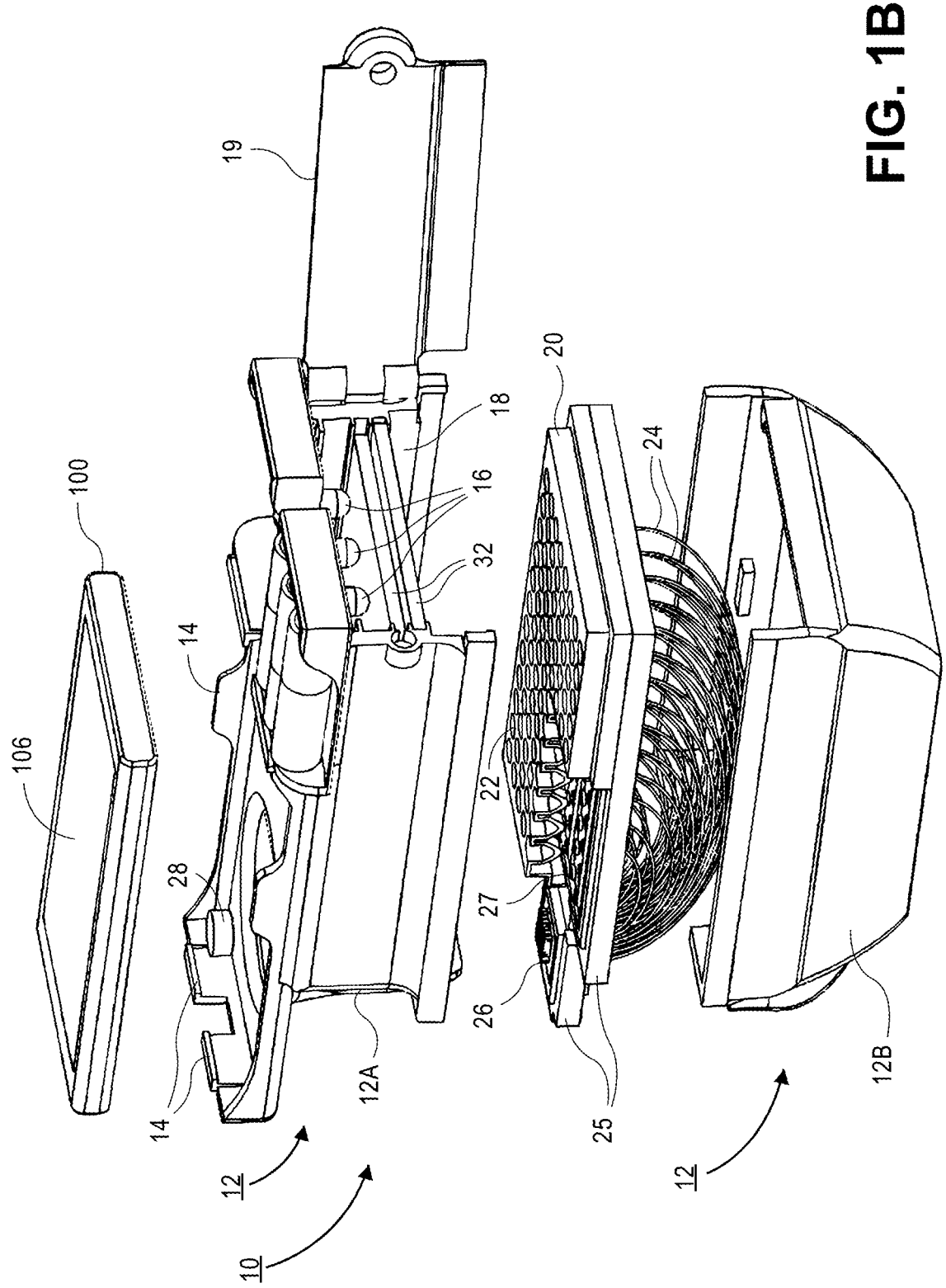
FIG. 1B illustrates an exploded, perspective view of the hand-held micro-plate reader of FIG. 1A.
Figure 1C:
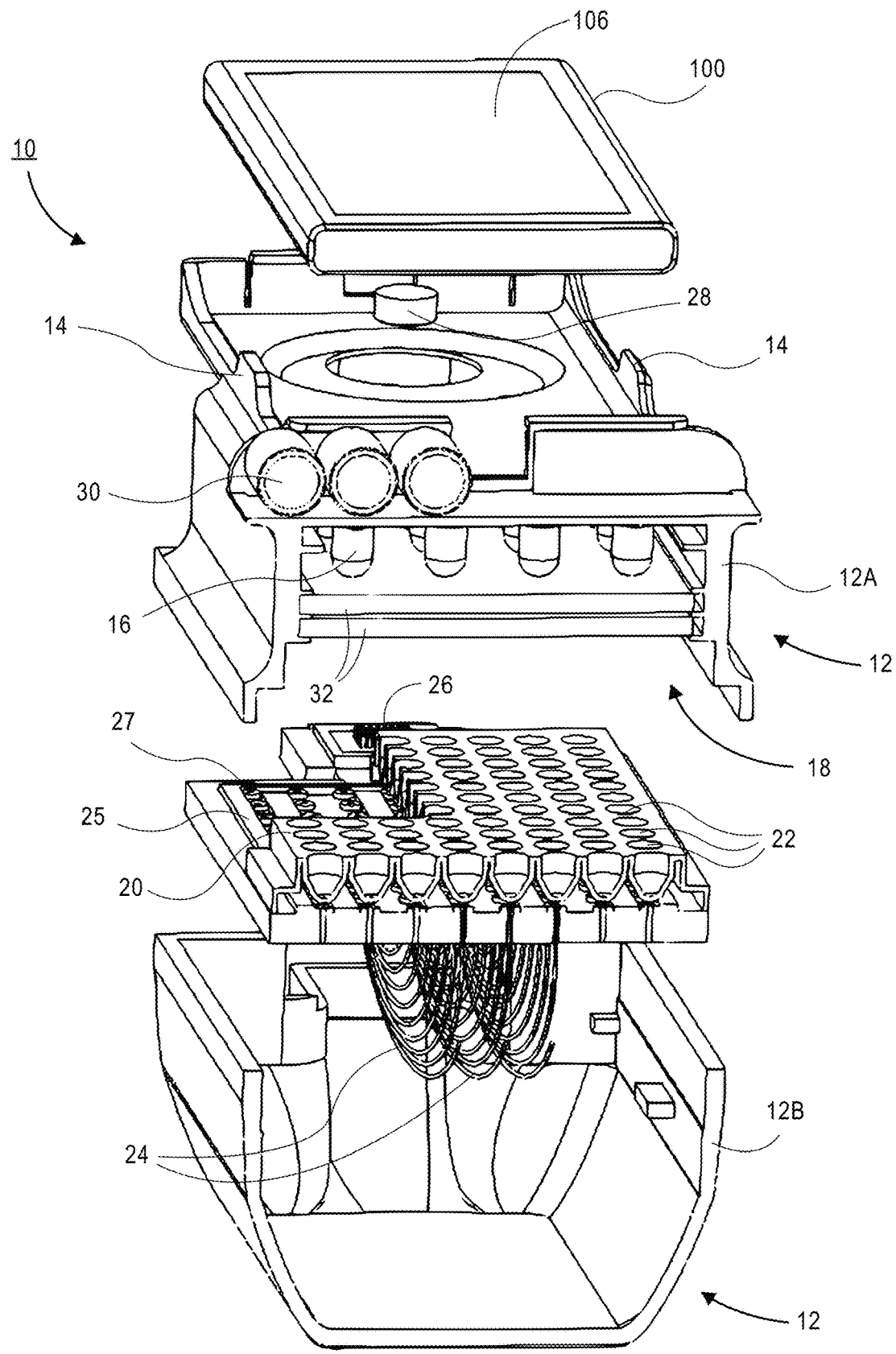
FIG. 1C illustrates a cross-sectional, exploded perspective view of the hand-held micro-plate reader of FIGS. 1A and 1B.

FIGS. 1A-1C illustrates an embodiment of the microplate reader 10 for use with a portable electronic device 100 having a camera 102 (FIG. 1E) therein. In this example, the portable electronic device 100 is a mobile phone or cell phone although the portable electronic device 100 may also include other portable electronic devices with a camera 102. These include, for example, tablet PCs, webcams, and digital cameras. The micro-plate reader 10 is, in one particular embodiment, portable and is hand-held (either with one or both hands depending on portable electronic device 100 being used). In one aspect of the invention, the portable electronic device 100 also has wireless functionality such that images and data may be transferred to a remote computer or server as explained herein. Wireless functionality may occur over a WiFi network that is connected to the Internet. Alternatively, wireless functionality may be provided on a mobile phone network. Bluetooth wireless transfer may also be used to transfer data and images to a physically nearby yet separate remote computer.

Figure 1E:
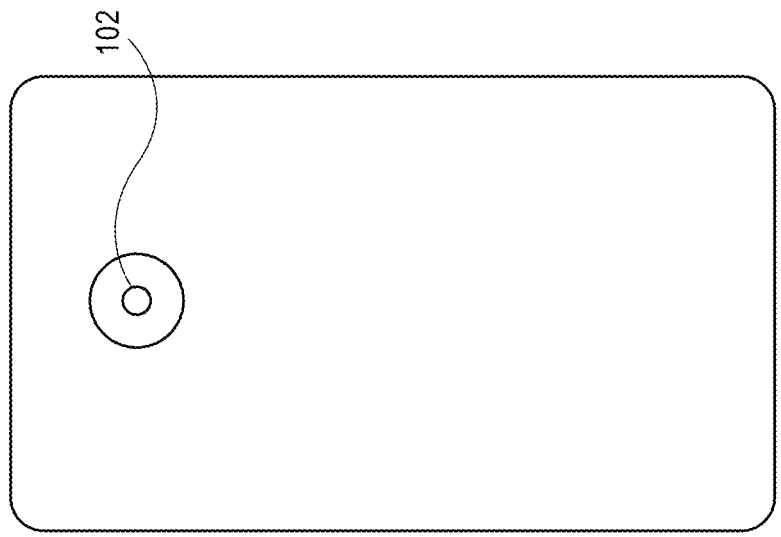
FIG. 1E illustrates a back view of a portable electronic device (e.g., mobile phone) according to one embodiment.
Figure 1D:
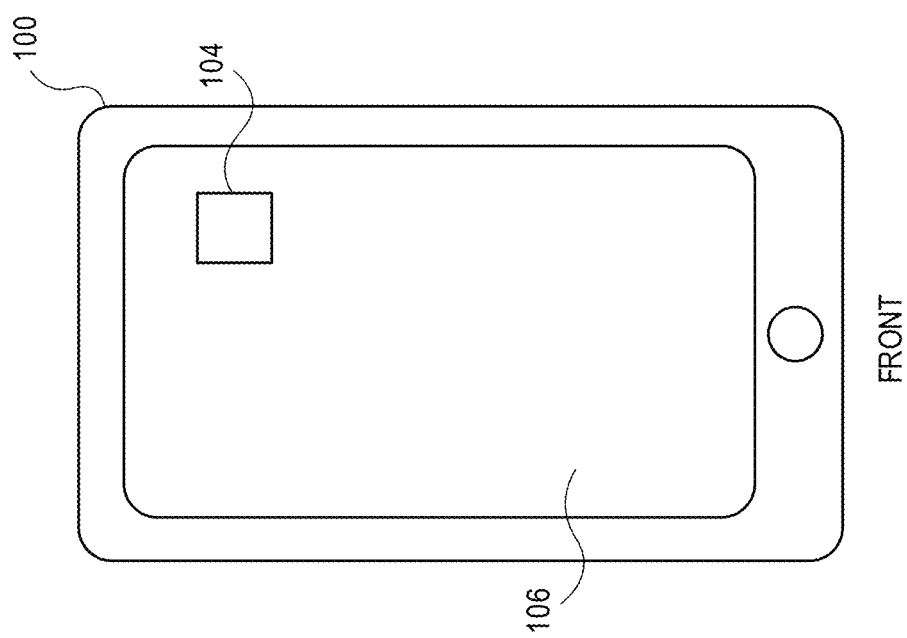
FIG. 1D illustrates a front view of a portable electronic device (e.g., mobile phone) according to one embodiment.
Figure 2:
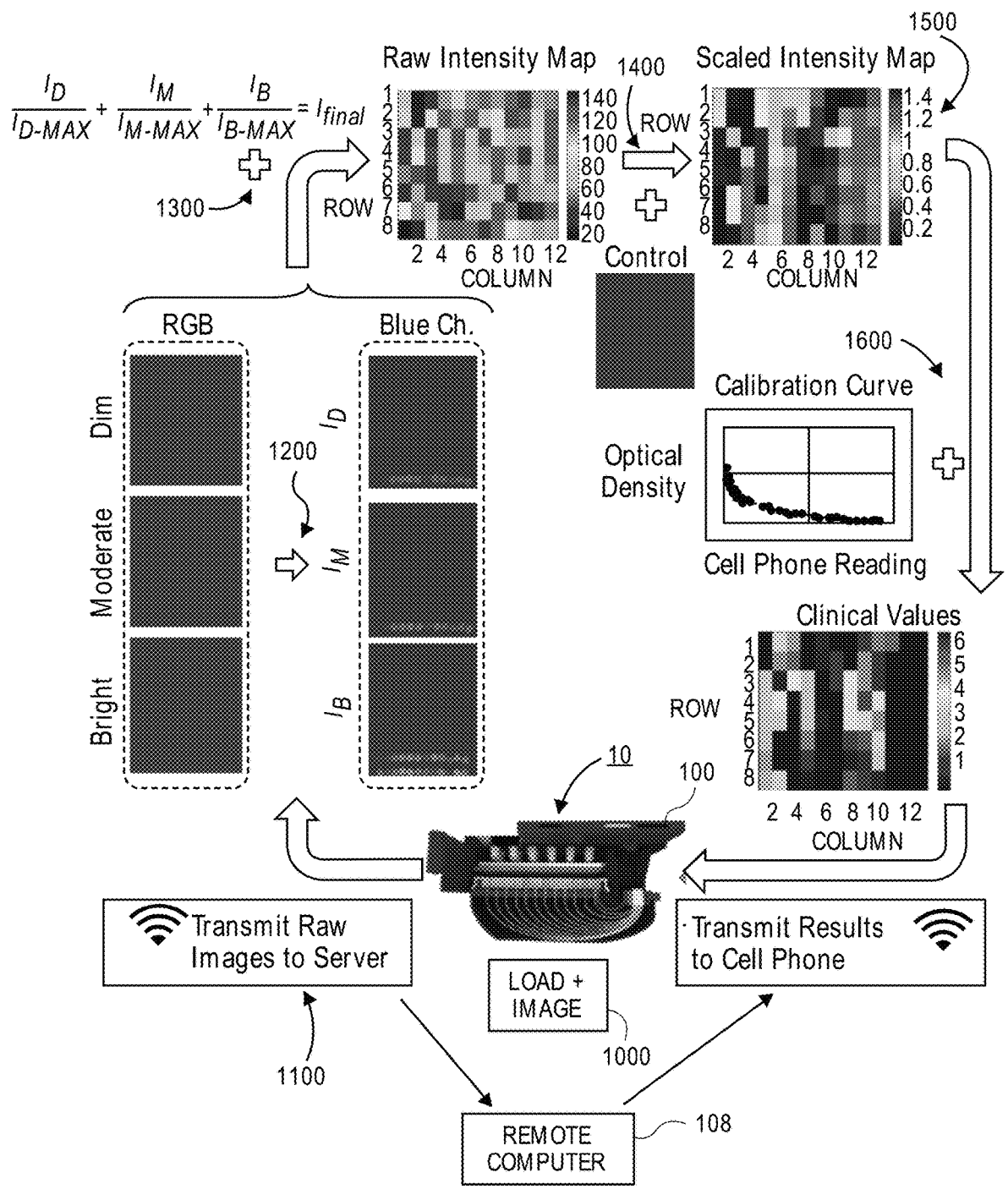
FIG. 2 illustrates a flow chart showing the operations for data processing that takes place during a test using the hand-held micro-plate reader of FIGS. 1A-1C.

In one embodiment of the invention, the portable electronic device 100 includes software or an application 104 (FIG. 1D) that runs on the portable electronic device 100. A user may interface with the application 104 using a graphical user interface (GUI) that is displayed on the display 106 (FIG. 1$_D$) of the portable electronic device 100. The application 104 may be used by the user to run the colorimetric test, transfer data and image files to a remote computer (optional), receive data from the remote computer (optional). In other embodiments as described herein, image processing and data analysis may occur exclusively on the portable electronic device 100 in which case there is no need to transfer/receive data and images to a remote computer. Of course, this option may require additional computation resources that might not be available on all portable electronic devices 100. Thus, the invention described herein further contemplates an embodiment where images that are obtained using the portable electronic device 100 are transferred to a remote computer 108 as illustrated in FIG. 2 or a local computer 120 such as that illustrated in FIG. 9 for image processing and data analycic.

As seen in FIGS. 1A-1C, the micro-plate reader 10 includes an opto-mechanical attachment 12 that is configured to attach/detach to the portable electronic device 100.

As seen in the exploded views of FIGS. 1B and 1C, the opto-mechanical attachment 12 may be formed from multiple parts. An upper part 12A, which is secured to the portable electronic device 100 contains the power source 30, illumination sources 16, optical diffusers 32 defines a slot 18 that is used to receive an optically transparent plate 20. A lower part 12B is secured to the upper part and covers the lower portion of a base plate and provides space for the optical fibers described herein. The upper part 12A of the opto-mechanical 12 attachment may include one or more fasteners 14 such as tabs, clips, or the like that are used to removably fasten the opto-mechanical attachment 12 to the portable electronic device 100. As seen in FIGS. 1A-1C, the opto-mechanical attachment 12 is secured to the "back" side of the portable electronic device 100 (e.g., the back of the mobile phone that has the camera 102 located on the back as seen in FIG. 1E) leaving the display 106 unobstructed so that it can be used while the opto-mechanical attachment 12 is secured thereto. The opto-mechanical attachment 12 may be made from a number of different materials although polymer based materials provide for a sturdy yet lightweight construction. The opto-mechanical attachment 12 may be designed specifically to fit a particular brand or model of portable electronic device 100. Alternatively, the opto-mechanical attachment 12 may include one or more adjustable fasteners 14 or the like such that a single version of the opto-mechanical attachment 12 may be used on different makes and models of portable electronic devices 100 which have different sizes and different locations of the camera 102. The opto-mechanical attachment 12 defines a housing that contains the various components required for the illumination of the micro-plate as well as the optical components required to transmit collected light to the camera of the portable electronic device 100.

The micro-plate reader 10 includes a plurality of illumination sources 16 that used to illuminate the micro-wells 22 as explained herein. In one preferred embodiment, the plurality of illumination sources 16 are configured as an array of illumination sources. For example, for the experiments described herein, the plurality of illumination sources 16 was an array of twenty-four (24) blue light emitting diodes (LEDs). Alternatively, laser diodes may be used. While blue colored light was emitted it should be appreciated that other colors could be used. The micro-plate reader 10 includes a slot 18 that is dimensioned to accommodate an optically transparent plate 20 that contains an array of wells 22 contained therein. The slot 18 may be exposed or closed using a hinged door 19 (FIGS. 1A and 1B) that is opened to insert or remove the optically transparent plate 20. The door 19 is closed when imaging is performed. The optically transparent plate 20 contains an array of wells 22 that are typically arranged in rows and columns. For example, a common configuration is the so-called 96 well plate which contains an 8×12 array of wells 22. Commercially available 96 well plates are readily available and, in some embodiments, may be used with the micro-plate reader 10 described herein. The slot 18 is dimensioned to have a depth and width to accommodate the optically transparent plate 20 with the array of wells 22. The slot 18 preferably is dimensioned so that, when fully inserted into the opto-mechanical reader 10, each well 22 is positioned adjacent to a separate optical fiber as explained below. Each well 22 is sized to hold a sample therein. For ELISA tests, the wells 22 are pre-prepared/treated with ELISA reagents. For example, 96 well plates that are premade for ELISA testing are known and commercially available. These plates can be used in conjunction with the micro-plate reader 10.

As seen in FIGS. 1B and 1C, the housing of the opto-mechanical attachment 12 includes a plurality of optical fibers 24. Each optical fiber 24 of the plurality includes two ends. A first end of each optical fiber 24 is secured in position such that when the optically transparent plate 20 is inserted into the slot 18 of the micro-plate reader 10, the first end is located at or adjacent to one of the wells 22 located in the optically transparent plate 20. In one aspect of the invention, the opto-mechanical attachment 12 includes a base plate 25 that is used to secure the first ends of the optical fibers 24. The base plate 25 has a plurality of apertures 27 formed therein that receive the first ends of the optical fibers 24. The optical fibers 24 are secured in the apertures 27 and collectively define an input array of optical fibers. The optical fibers 24 can be secured to the base plate 25 using glue, adhesive, or other bonding material. While FIG. 1C illustrates a single aperture 27 associated with each well 22 that contains a single fiber 24, there could be multiple apertures 27 associated with a single well 22 such that multiple fibers 24 carry the light from a single well 22 (or multiple fibers 24 could even be secured in a single aperture 27 to achieve the same result). The location of the apertures 27 in the base plate 25 is arranged to correspond to the location of the wells 22 in the optically transparent plate 20 (See FIG. 3). For example, for a 96-well plate, there are 96 apertures 27 or holes that are formed in the base plate 25 for receiving the first ends of the optical fibers 24 with each aperture 27 or hole positioned so that it is substantially centered on the well 22 when the optically transparent plate 20 is placed in the slot 18. The base plate 25 defines a bottom surface of the slot 18 and when the optically transparent plate 20 is placed on top of the base plate 25 when loaded into the opto-mechanical attachment 12.

Figure 3:
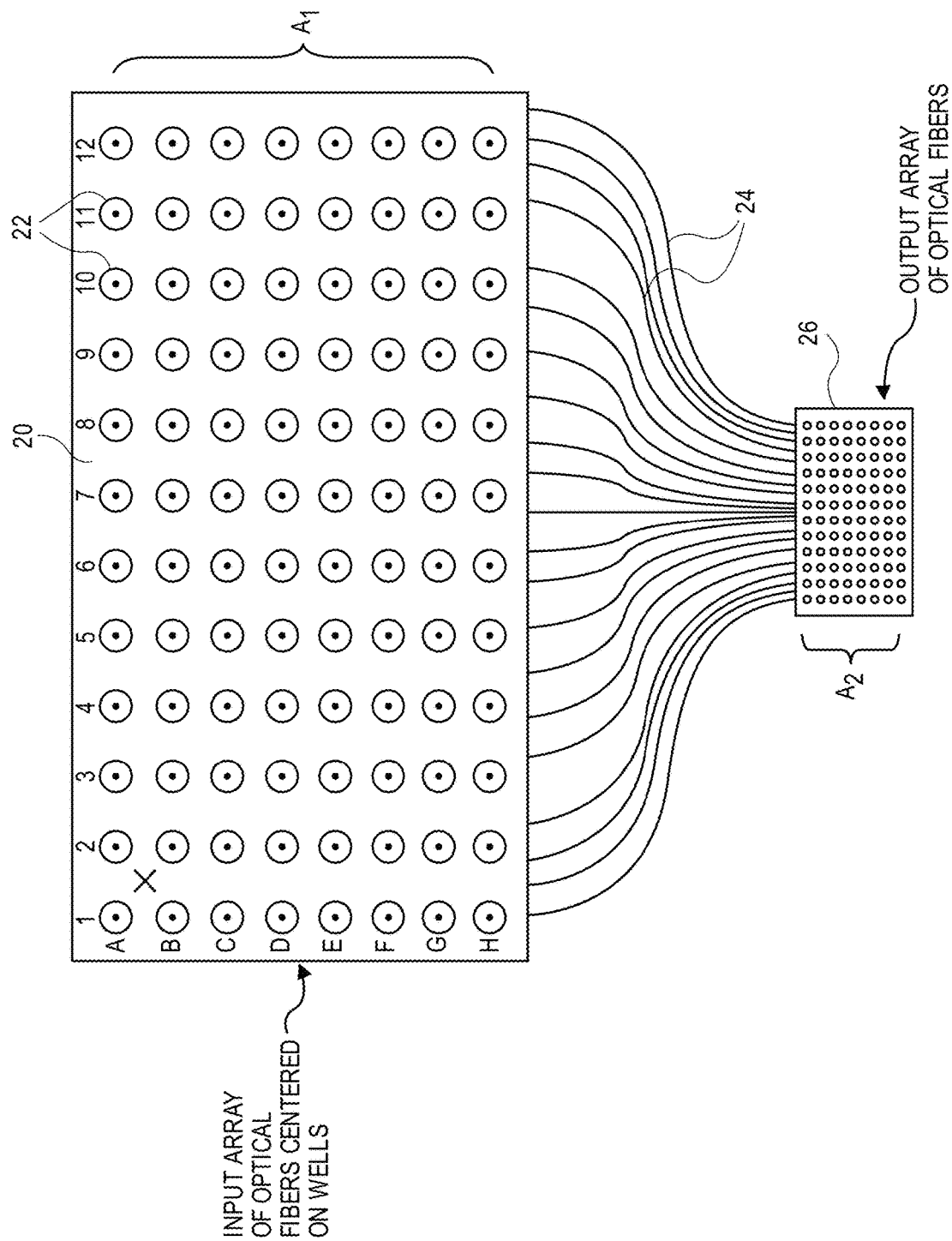
FIG. 3 illustrates a top down plan view of an optically transparent plate along with a header containing an array of optical fibers (e.g., output array of optical fibers). The area of the optical fiber array in the header $A_2$ is at least 10 times smaller than the area $A_1$ of the wells in the optically transparent plate. Each well has a one or more optical fibers associated with it that is substantially centered on each well. The ends of the fibers located adjacent to the bottom of the walls define an input array of optical fibers.

The second or opposing end of the optical fiber 24 is secured to a header 26 formed in the base plate 25 to form an output array of optical fibers 24 therein. The header 26 is used dramatically increase the density of optical signals generated from the wells 22. In particular, the output array of optical fibers 24 in the header 26 has a cross-sectional area $A_2$ (as seen in FIG. 3) that is at least ten times (i.e., 10×) less than the cross-sectional area $A_1$ of the input array of optical fibers 24 that are formed in the base plate 25 (the cross-sectional area $A_1$ may also be referred to as the cross-sectional area of the wells of the optically transparent plate). Another way of saying this is that the density of "virtual" wells that is created at the header 26 by the array of optical fibers 24 is at least ten times as large as the density of actual wells 22 in the optically transparent plate 20. Still referring to FIGS. 1B and 1C, the opto-mechanical attachment 12 includes a lens 28 therein. The location of the lens 28 is such that the lens 28 is interposed in an optical path formed between the array of optical fibers in the header 26 and the camera 102 of the portable electronic device 100. The lens 28 is secured in position in the upper half 12A of the opto-mechanical attachment 12. Thus, the light that exits the array of fibers 24 in the header 26 passes through the lens 28 prior to reaching the camera 102 of the portable electronic device 100. In some alternative embodiments, the lens 28 may be omitted entirely. For example, depending on the size of the attachment and the focal length of the camera 102

Still referring to FIGS. 1A-1C, a power source 30 is disposed on or in the opto-mechanical attachment 12. The power source 30 may include a number of batteries such as AAA batteries or the like. The power source 30 can be switched on or off using a conventional switch or the like (not shown). A current regulator (not shown) may be included in the power circuit for the LEDs making up the illumination sources 16. Alternatively, the portable electronic device 100 may provide power to the opto-mechanical attachment through a cable or other connection. To maximize uniform illumination of the optically transparent plate 20 containing the wells 22, the individual light sources 26 may be centered against four (4) wells 22 as illustrated by position "X" in FIG. 3. Illumination from the light sources 26 is further homogenized using one or more diffusion layers 32 (in FIGS. 1B and 1C the diffusion layers are illustrated as only traversing part of the way over the optically transparent plate 20 for clarity but in the working embodiment they extend all the way across). The one or more diffusion layers 32 may include plastic diffuser sheets that have areas that cover substantially all of the optically transparent plate 20.

FIG. 3 illustrates how optical fibers 24 are used in the opto-mechanical attachment 12 to generate small, dense "virtual" wells based on the actual wells 22 in the optically transparent plate 20. Each well 22 has its own dedicated optical fiber 24 that is used to transmit light emitted from that well 22 to the array formed in the header 26. As an alternative to a single optical fiber 24 for each well 22, there may be multiple optical fibers 24 that are associated with each well 22 (e.g., a single optical fiber bundle made of multiple fibers 24 is associated with a single well 22). The header 26 contains an array of fibers 24 that maintains the same row and column configuration as the actual wells 22 in the optically transparent plate 20. For example, FIG. 3 illustrates a 96-well plate array that has 12 columns and 8 rows (or vice versa depending on the orientation). This same column/row is preserved in the array of optical fibers 24 at the header 26. That is to say, the header 26 includes an array of optical fibers 24 that also has 12 columns and 8 rows.

FIG. 4A illustrates a top down view of an example of an optically transparent plate 20 in the form of a 96-well plate array that can be used with the micro-plate reader 10 described herein. FIG. 4B illustrates a photographic image that is obtained from camera 102 of the portable electronic device 100. Note how the rows and columns of the image of FIG. 4B correspond with the rows and columns of the actual 96-well plate array.

FIG. 2 illustrates a flow chart illustrating the flow of data processing that is used according to one aspect of the invention to generate qualitative and/or quantitative clinical results. As seen in operation 1000, the optically transparent plate 20 loaded with sample(s) is loaded into the opto-mechanical attachment 12 and the illumination sources 16 are turned on and images are acquired using the camera 102 of the portable electronic device 100. Images are captured at three different exposure times (dim($\tau_D$) 1/1600 s, moderate ($\tau_M$) 1/1250 s, and bright($\tau_B$) 1/800 s). The application 104 may be used to acquire these images or other image programs can be used to capture the images. In the experimental results described herein, a Nokia Pro Camera application was used and the resulting images were saved on the mobile phone using the RAW DNG image format (7152×5360 pixels).

Figure 5C:
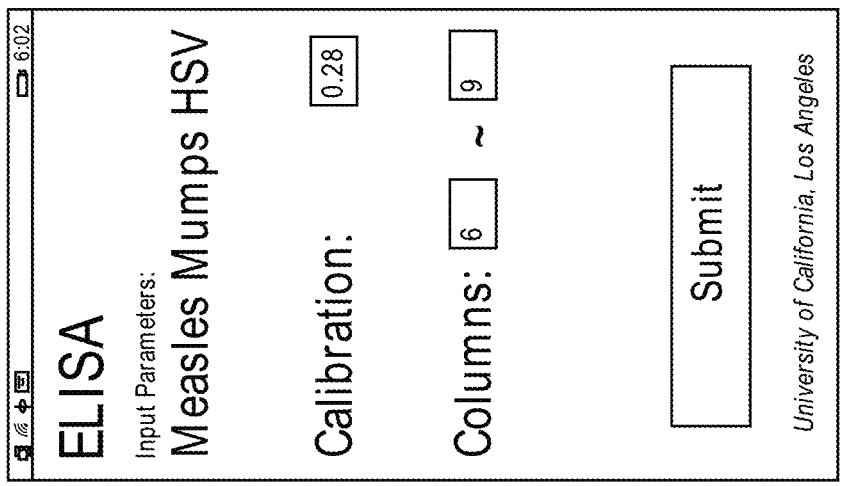
Figure 5B:
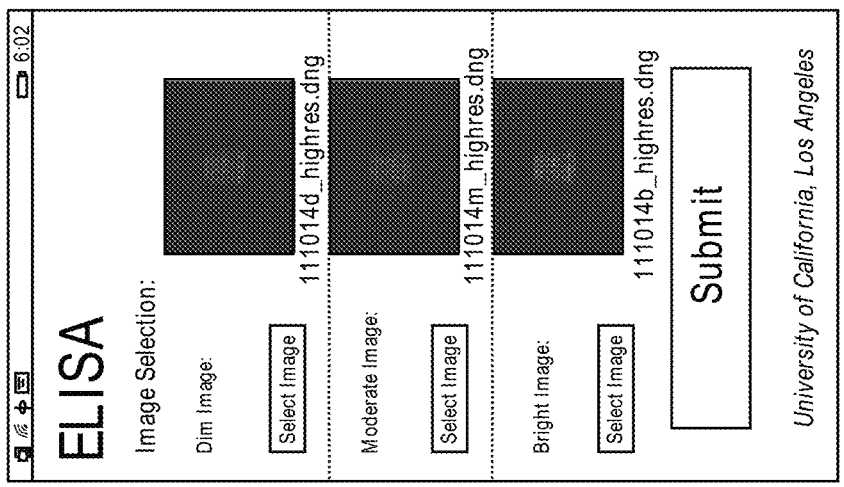
Figure 5A:
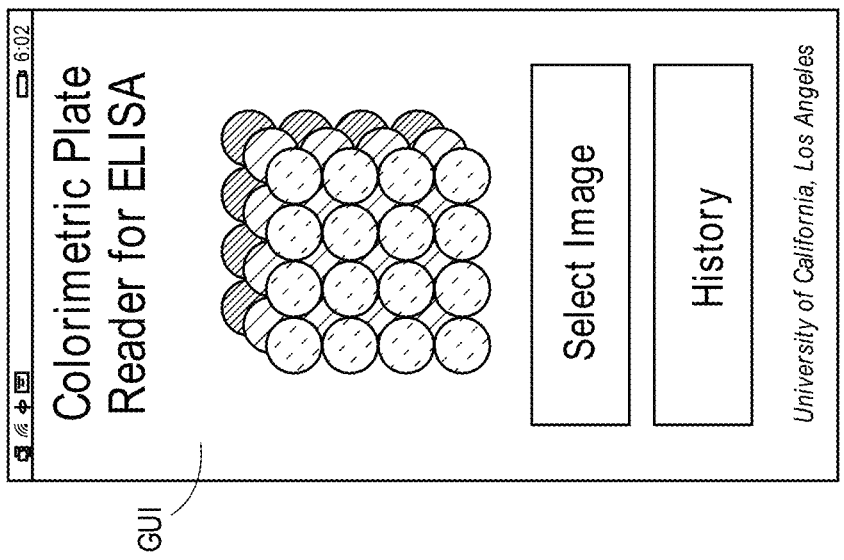

To process the images, the application 104 that is contained in the portable electronic device 100 is executed or run. FIGS. 5A-5F illustrate illustrative screen shots of the GUI presented to the user that is used to analyze the samples contained in the wells 22 of the optically transparent plate 20. With reference to FIG. 5A, the user is able to select from the main menu the images that will be analyzed. This may include images generated during a current or new test or review previous tests (e.g., history button as seen in FIG. 5A). FIG. 5D illustrates, for example, prior tests that have been performed on micro-plate reader 10. These tests may be selected and results viewed as illustrated in FIGS. 5E and 5F. When starting a new test, the user first selects the dim, moderate, and bright images to use as seen in the GUI illustrated in FIG. 5B. Next, as seen in FIG. 5C the user specifies the type of each immunoassay being tested (e.g., measles IgG, mumps IgG, HSV1 or HSV2 IgG), the column location of the tests in the wells 22 of the optically transparent plate 20, and any conversion factors (e.g., calibration values or parameters) provided by the kit manufacturer, and then submits the test to the server for processing. In this particular embodiment, the image processing is offloaded to a remote computer 108 rather than being processed on the portable electronic device 100. Thus, referring back to FIG. 2, images are transmitted to the remote computer 108 which may take the form a computer server as seen in operation 1100. As an alternative to a remote computer 108 such as a server, the images may also be transferred to a local computer such as a separate but local computer such as computer 120 in FIG. 9.

After receiving this new test request, the remote computer 108 waits for the image test files to finish uploading before processing (experiments were run in Python using Twisted framework—although other implementations may be used). In the experiments described below, the DNG images are first converted to tagged image file format (TIFF) for easier extraction of the blue channel of the image. The blue channel pixel intensities are then extracted in operation 1200 from the raw images by localizing the Bayer pattern and defining its orientation. From the blue channel extracted image, the average pixel intensity of each individual well 22 is obtained. To do so, the centroids of each well 22 are automatically detected using a custom designed image processing algorithm. Since some centroids will randomly have low light intensity, a basic intensity thresholding method is not sufficient to accurately determine the position of all the 96 wells. Therefore, the custom-designed algorithm finds two reference centroids as plate 20 markers using pixel intensity thresholding in combination with morphological erosion-dilation operations to separate overlapping wells 22. In the algorithm the upper rightmost and the lower rightmost wells 22 are selected as reference centroids, and using their respective coordinates, the algorithm is able to match the positions of all the remaining centroids by performing alignment/rotation corrections on the 96 previously calculated blank plate centroids. Once these centroids are detected, a circular mask with a 15 pixel radius, which is a few pixels smaller than the radius of the actual well 22, is used to prevent edge related artifacts in data processing.

Once the blue channel information is extracted, the dim, moderate, and bright average intensities per well 22 (i.e., $I_D$, $I_M$, and $I_B$, respectively) are combined to produce a high dynamic range (HDR) image (value between 0 and 255). This is achieved through the addition of each intensity after being scaled by the brightest well for that exposure time as seen in operation 1300, where $I_{D-MAX}$ is the highest well intensity of all the wells in the dim exposure time $\tau_D$; $I_{M-MAX}$ and $I_{B-MAX}$ follow the same convention. To normalize against imaging system-induced changes on e.g., well transmittance, blank reference wells with de-ionized (DI) water were also imaged, which is a step performed only once for a given reader. This is illustrated in operation 1400 of FIG. 2. After this normalization step, each cell in the scaled intensity map is scaled between a value between 0 and 1 as seen in operation 1500 of FIG. 2. Using this scaling convention, a 1 represents complete transmittance relative to DI water control, while a 0 represents no transmittance reading. Note that some wells may have values that exceed 1 which means such wells transmit more light than the control (an example would be a well that is not used). This can be seen in some well values for columns 11 and 12 in FIG. 2. These wells, however, do not produce positive clinical values as indicated as seen by the clinical value well map of FIG. 2.

The last step in the processing is to convert the optical density (OD) or transmittance values to a quantified index value used for clinical decisions. This conversion from OD to clinical index value is defined by the manufacturer of each immunoassay and is seen in operation 1600 of FIG. 2. The parameters used for this conversion to the final quantitative index value are the optical densities of three calibration wells 22 used in the 96-well plate and a test specific pre-determined conversion factor (as seen in FIG. 5C). FIG. 2 illustrates a calibration curve for the optical density measurements as a function of mobile phone measurements. Finally, a matrix of these quantified clinical index values (one for each well) is transmitted back to the portable electronic device 100 for the user to view through the same application 104. The results of the analysis can then be presented to the user and displayed on the display 106. FIG. 5E illustrates qualitative results of an exemplary test run for both measles and mumps. Measles results are in rows 6-9 while mumps results are in rows 10-12. In this particular example, "N" represents a negative result while "P" represents a positive result. FIG. 5D illustrates the quantitative results of this same experiment showing measured clinical values.

For the process of making qualitative clinical determinations such as those illustrated in FIG. 5E, two different methods may be used. The first method applies a threshold identical to the threshold of the original ELISA assay but this threshold is based on the clinical index values obtained by the micro-plate reader 10. For example, a clinical index value between 0.9 and 1.1 results in an equivocal determination, negative below 0.9, and positive above 1.1. Separate to the curve-fitting and threshold based diagnostic approach, a machine learning algorithm may be employed to make clinical determinations using a total of 58 spatial features that are automatically extracted from the images acquired by the portable electronic device 100. This second approach, which is illustrated in FIG. 6, makes no assumptions of a calibration function and increases its diagnostic accuracy as training sample size increases.

Figure 6:
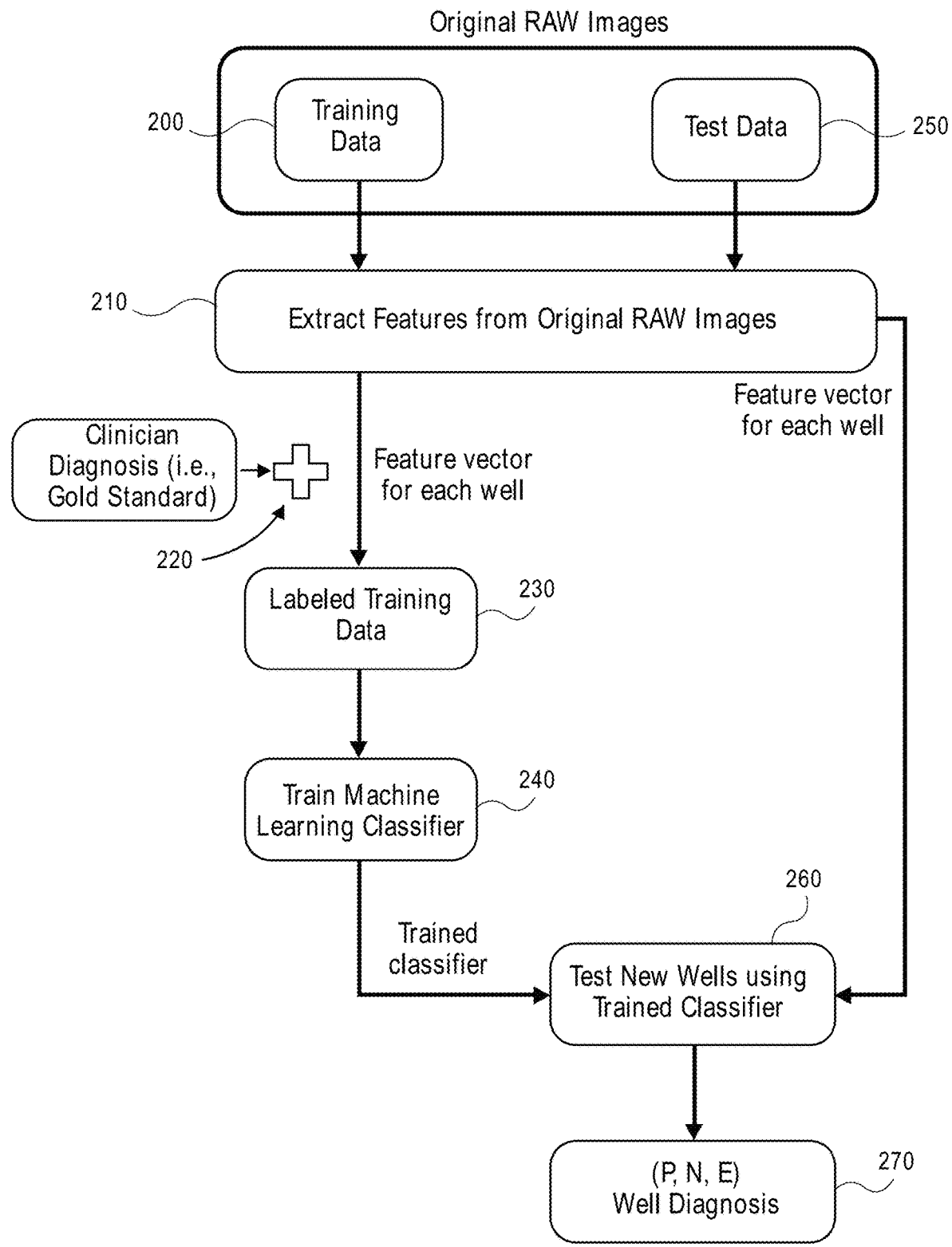
FIG. 6 illustrates a process flow diagram for a process that uses machine learning to generate qualitative diagnostic results of a sample according to one optional aspect of the invention. The machine learning option is an alternative to using standard thresholding of calibrated optical density values.
Figure 7A:
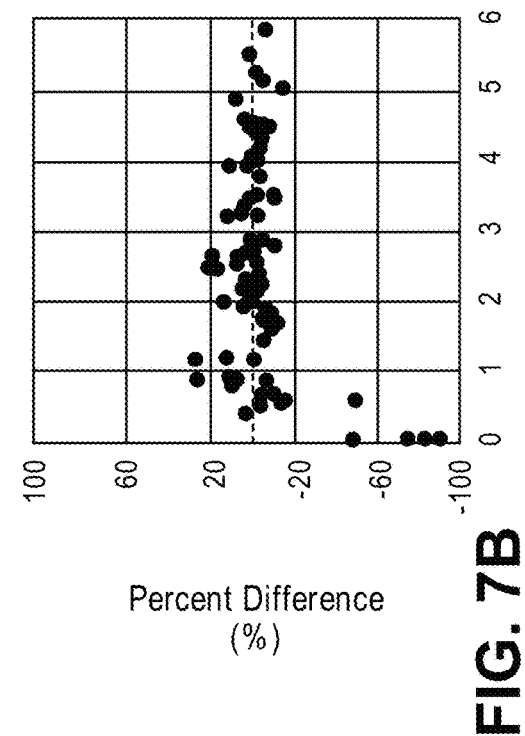
FIGS. 7A-7H illustrate the mobile phone reader results obtained for these ELISA tests (mumps, measles, HSV1, HSV2).
Figure 7B:
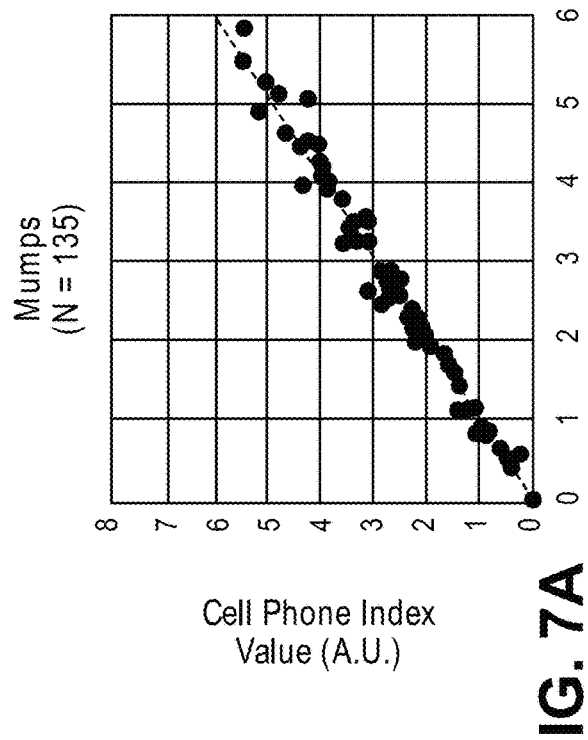
Figure 7C:
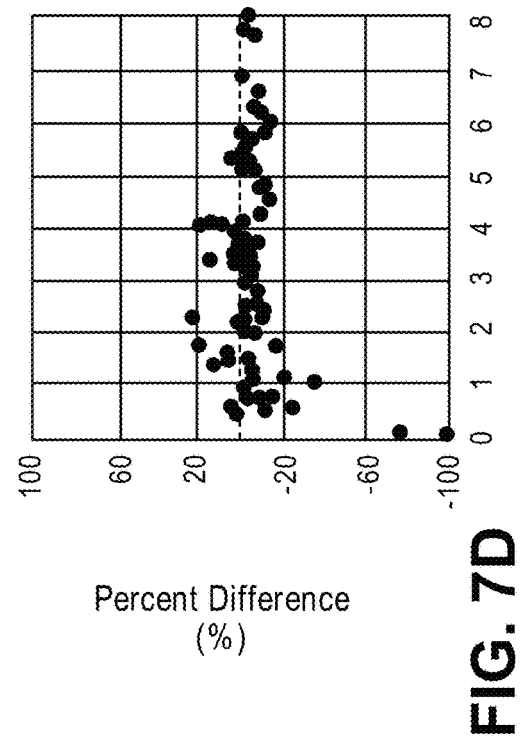
Figure 7D:
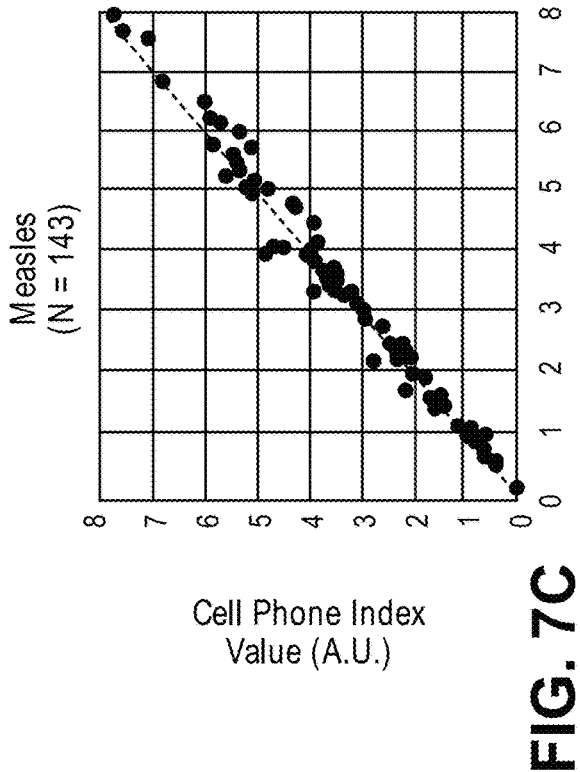
Figure 7E:
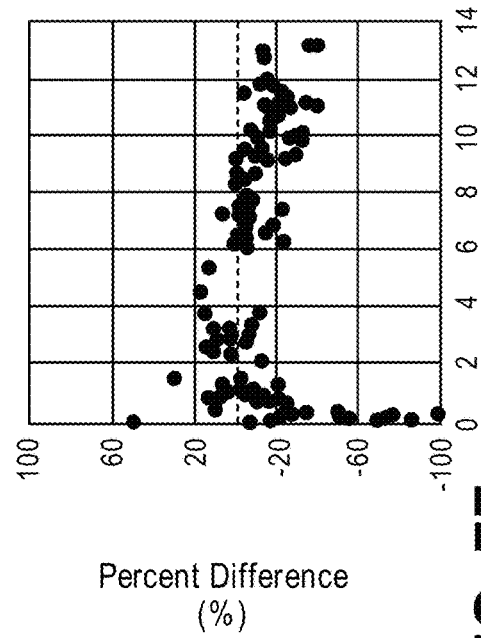
Figure 7F:
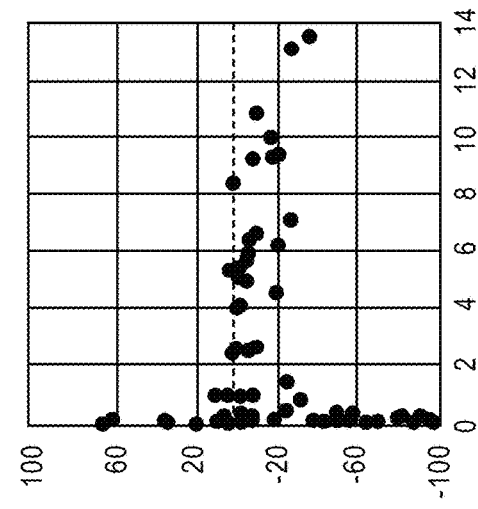
Figure 7G:
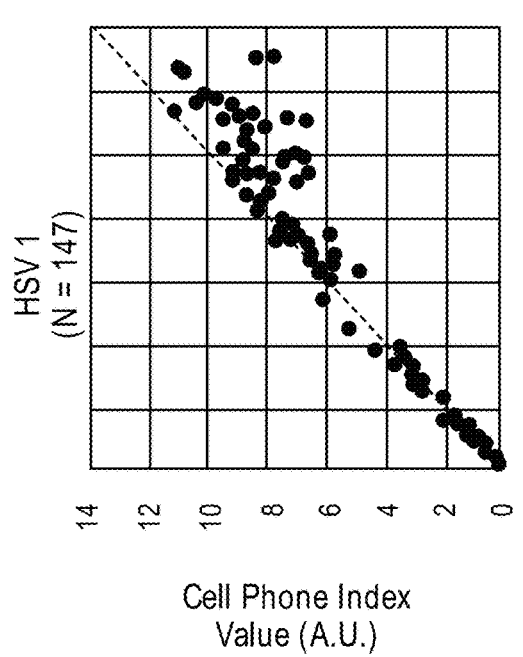
Figure 7H:
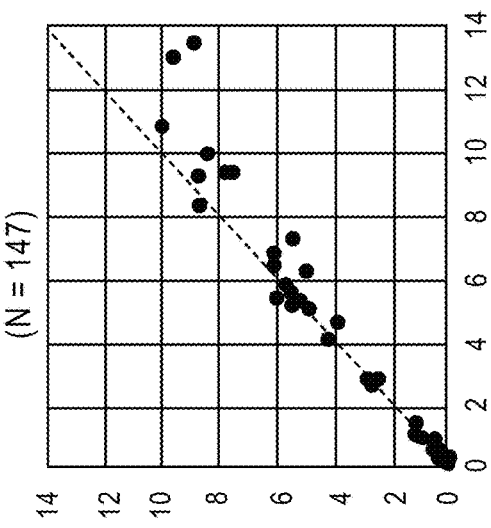

With reference to FIG. 6, the goal of the machine learning framework is to estimate the correct diagnostic label corresponding to each test set and every time a new test is performed, a test data set is created by extracting the same spatial features used for the training data set. An adaptive boosting machine learning algorithm was used, which statistically learned from the training data set and estimated a diagnosis from each entry contained in the test data. Adaptive boosting machine learning may be found in O. M. Mozos et al., in Proceedings of the 2005 IEEE International Conference on Robotics and Automation, pp. 1730-1735 (2005), which is incorporated by reference herein. This algorithm provides accurate diagnosis by establishing statistical relations between the spatial features of the training data set and gold standard diagnostic labels (e.g., negative, equivocal, or positive). These statistical relationships are then applied to the features of the test data to make blind diagnostic decisions. The main advantage of using adaptive boosting based machine learning algorithms is its capability to detect the most promising features and discard others that may degrade the accuracy of the results. Consequently, the dimensionality of the statistical model is reduced and the accuracy of the final predictions is boosted.

Experimental

In the experimental results described herein, the micro-plate reader system used a Windows based smartphone (Lumia 1020, Nokia), paired with a portable 3D printed opto-mechanical attachment to package together optical components, and a cloud connected data processing server (i.e., remote computer) in communication with a custom mobile application that serves as an interactive user interface. The hand-held nature of the micro-plate colorimetric reader allows for use in the field, away from sophisticated machinery, but the data processing speed is partially limited by the computational hardware and the software available for use on the mobile phone. To resolve this partial limitation while also maintaining portability, a remote server was used for data processing and a wireless network (e.g., cellular data, Wi-Fi) for data transfer between the server and the mobile application as seen in FIG. 2.

The 3D printed embodiment of the micro-plate reader included three separate parts: the top part, which primarily functions as the holder for the mobile phone, the bottom of the device, which houses the fiber optic array, and the middle chamber which is used to load a 96 well plate, which was illuminated vertically by an LED array contained therein consisting of twenty-four (24) uniformly distributed blue LED's (peak wavelength, 464 nm). This system was powered using six (6) AAA batteries and there is a low-noise, low-dropout linear current regulator in the system that provides constant power to all 24 LEDs. To maximize the uniformity of the illumination from the LED array, each LED is centered against 4 wells on the plate ("X" position in FIG. 3), and the illumination light was further homogenized by passing through two layers of plastic diffusers before reaching the plate. During each test, the 96-well ELISA plate of interest is inserted through the back slot of the device. Blue light is transmitted through each well and is then coupled into the optical fibers, which guide the transmitted light to the header which contains the optical fibers but in a tight fit with a much smaller (more than 10× smaller) cross-sectional dimension than the 96 well plate. The optical fibers in the header emit light to the external collection lens (focal length 45 mm in the experimental embodiment) that is placed in front of the mobile phone camera. This fiber-optic imaging geometry yields a demagnification factor of approximately 11-fold within a rather compact and folded imaging design, which significantly reduces the height of the entire reader.

The transmitted light through this fiber optic array was captured using the mobile phone camera (41 megapixel, pixel size of 1.12 µm) in a RAW 10-bit/channel Digital Negative (DNG) image format. FIG. 4B shows an example of an image taken by the system. The sample plate corresponding to this image is also shown in FIG. 4A. The overall dimensions of the mobile reader are ~195×98×100 mm.

FIG. 2 illustrates how raw photo images and results are communicated between the mobile phone and the remote server, and the flow chart of data processing carried out in the server to obtain the final clinical quantitative values. First, the ELISA plate is inserted into the reader device and images are captured at three different exposure times (dim ($\tau_D$) $\frac{1}{1600}$ s, moderate($\tau_M$) $\frac{1}{1250}$ s, and bright ($\tau_B$) $\frac{1}{800}$ s) using the Nokia Pro Camera application and saved on the phone using the RAW DNG image format (7152×5360 pixels). To process these images, the user runs the application that is executed on the mobile phone as described herein.

Clinical Test Results

The colorimetric mobile phone based system has shown the ability to reach high accuracy levels, ~99-100%, for the detection of measles IgG, mumps IgG, HSV-1 IgG and HSV-2 IgG, with a total runtime of ~1 min on the server (Intel Core i5-760, 2.8 GHz, 16 GB RAM) per each 96-well plate. FIGS. 7A-7H shows the mobile phone reader results obtained for these ELISA tests (mumps, measles, HSV1, HSV2). FIGS. 7A, 7C, 7E, 7G illustrate the mobile phone index value versus the reference index value (both in arbitrary units), while the FIGS. 7B, 7D, 7F, and 7H expresses the error detected between the results obtained by the mobile system and the gold standard, which is an FDA-approved clinical spectrophotometer. On each graph the clinically relevant linear-response region of each test, determined by their manufacturer, is also indicated (shaded region).

Looking at the plots of the reference index value versus the mobile phone measured index value shown in FIGS. 7A, 7C, 7E, 7G, one can see that there is a strong correlation between the two readings and that there is an overlap, as expected, in the region of linearity between the two methods (shaded portion). The percentage difference plots shown in FIGS. 7B, 7D, 7F, and 7H also illustrate that, as desired, there is no concentration dependent bias between the two measurement methods. Furthermore, outside of the highlighted shaded ranges shown in FIGS. 7A-7H a linear response is not expected for any read-out method or instrument, and that is why the deviation of the correlation between the mobile phone based measurements and the reference method is not significant from the perspective of diagnostic classifications/decisions. In fact, as summarized in Table 1 below, by using thresholds in the clinical index value space, where C<0.9, C>1.1 and 0.9<C<1.1 define negative, positive and equivocal samples, respectively, one can achieve very strong agreements in the diagnostic decisions for all the tests against the gold standard well plate reader.

These results can be further improved by analyzing the spatial features of the acquired images using a machine learning algorithm as detailed herein. Indeed, Table 1 reports the significant improvements that were achieved in overall accuracy, specificity and sensitivity of the diagnostic decisions by replacing simple threshold based decisions with machine learning analysis, which take into account fifty-eight (58) spatial features for each test well to arrive at a statistically trained and optimized ternary diagnostic decision.

According to Table 1, for mumps IgG samples, the machine learning algorithm achieves a 99.61% agreement to the FDA approved reference method. For measles samples, the agreement percentage is 98.56%. Similarly, for HSV-1 IgG and HSV-2 IgG results, agreements of 99.42% and 99.41% were obtained, respectively. The sensitivity and specificity performance of the machine learning approach is also better than the curve fitting based threshold approach, reaching >99% for HSV-1 IgG and HSV-2 IgG tests. The relatively lower specificity of mumps IgG (97.37%) and measles IgG (94.56%) tests obtained from the machine learning approach can be partially attributed to the smaller sample sizes in these tests compared to HSV-1 IgG and HSV-2 IgG tests.

Using a mobile phone with a camera and the 3D printed designed opto-mechanical attachment to illuminate and image a standard 96 well plate therein, an overall accuracy of ~99% was achieved or higher for HSV 1 IgG, and 99.4% for HSV 2 IgG tests. These results illustrate that the handheld and cost-effective system is able to match the performance of a conventional FDA-approved ELISA reader and give accurate diagnostic results to the users in approximately 1 min. Following the same calibration and testing procedures detailed in the Materials and Methods Section, the system should be able to achieve similar results for other diseases normally tested via standard ELISA techniques.

These results are especially timely considering the recent re-emergence of measles. The United States has shown a 600% increase in measles cases in 2014 due to lack of regular vaccinations. It is critical from a public health perspective to know exactly how many people are effectively protected from measles to avoid further outbreaks. The presence of measles IgG (as assayed in this study) above an FDA-defined threshold ensures protected status from this deadly reemerging disease. The availability of a handheld and cost-effective multi-well plate reader allows for high-throughput vaccine surveillance outside of centralized areas and at the point of care. This is also critical in an outbreak to rapidly determine the number of susceptible (IgG negative) people immediately exposed to an active measles case. Measles is highly contagious in unvaccinated individuals and can have a mortality rate as high as 1:1000.

The micro-plate reader reported herein could also expand vaccination testing to rural areas that do not have access to centralized testing laboratories with large scale spectrophotometers. The 96-well plate ELISA format is the gold standard for high throughput antibody screening due to the extreme cost savings associated with batch testing and

TABLE 1

| | Mumps | | Measles | | HSV 1 | | HSV 2 | |
| --- | --- | --- | --- | --- | --- | --- | --- | --- |
| | | | | N | | | | |
| | 133 | | 138 | | 151 | | 149 | |
| Analysis Type | Curve Fitting | M.L | Curve Fitting | M.L | Curve Fitting | M.L | Curve Fitting | M.L |
| Specificity | 92.70% ± 0.49% | 97.37% ± 2.63% | 92.09% ± 0.77% | 94.56% ± 3.43% | 100.00% ± 0.00% | 100.00% ± 0.00% | 100.00% ± 0.00% | 100.00% ± 0.00% |
| Sensitivity | 100.00% ± 0.00% | 100.00% ± 0.00% | 98.39% ± 0.42% | 99.47% ± 0.59% | 97.32% ± 0.32% | 100.00% ± 0.00% | 100.00% ± 0.00% | 100.00% ± 0.00% |
| Accuracy | 97.21% ± 0.41% | 99.61% ± 0.39% | 96.08% ± 0.32% | 98.56% ± 0.53% | 97.16% ± 0.55% | 99.42% ± 0.43% | 98.66% ± 0.22% | 99.41% ± 0.44% |

* Qualitative clinical results.
Percentages are shown with an error of one standard deviation.
M.L.: Machine Learning.

economics of scale compared to non-standard or non-batched cartridges or micro-chips. The micro-plate reader brings this capability to resource limited areas and makes high-throughput point of care ELISA testing a reality. In addition, this device could be immediately useful in support of large scale vaccination efforts in the developing world including trials and implementation of the tetravalent dengue vaccine. Such global health related efforts need to be coupled with a high-throughput, mobile and cost-effective ELISA screening device to ensure vaccine effectiveness and help eradicate disease.

In the experiments described herein, pipetting was used to load each well of the micro-plate of interest. Sample preparation and loading steps that are automated may be integrated onto the mobile phone based instrument. Microfluidic automation can now perform complex liquid handling steps powered by simply drawing a vacuum in a syringe, and commercial products have already integrated microfluidic systems into well plate formats. Low cost robotic liquid handler systems are also now becoming more commonplace, leveraging the consumer activities of the DIYBio and Maker communities and the prevalence of low cost microcontrollers (e.g., Arduino). The current focus on the optical readout automation, replacing bulky and expensive multi-well scanning spectrophotometers with a handheld design, addresses a key bottleneck in transitioning batched well-plate ELISA tests to field and resource poor settings, enabling standardization and economies of scale.

Materials and Methods

The colorimetric mobile phone-based micro-plate reader platform has been used in a clinical micro-biology lab to demonstrate detection of measles IgG, mumps IgG, HSV1 IgG and HSV2 IgG. For each disease, the performance of the tested approach was quantified by calculating accuracy, specificity and sensitivity values of the diagnostic decisions, where the results of an FDA approved well plate reader (DSX Automated ELISA system, Dynex Technologies, Chantilly, Va.) served as the gold standard. In order to minimize degradation of data quality due to elapsed time, all the clinical samples reported in this work were imaged by the mobile phone platform in less than 30 minutes after the same sample was analyzed by the benchtop commercial plate reader. All these experiments were performed at UCLA Clinical Microbiology Laboratory by medical personnel who did not develop the platform but was trained on how to operate the platform. For the performance calculations and comparisons, accuracy is defined as the number of true positives and true negatives divided by the total number of positives and negatives. Sensitivity is calculated as true positives divided by true positives plus false negatives, and specificity is calculated as true negatives divided by true negatives plus false positives. Note that since the gold standard technique sometimes is not able to accurately determine a positive or negative diagnosis, the equivocal test results of the reference technique are removed from the performance calculations, since these individual measurements do not present clinically interpretable results.

Calibration and Calculation of Teat Results

For calibration of the micro-plate reader device, ELISA wells with known OD values were used. A comparison of mobile phone reading values (C) versus true OD values obtained by the bench-top plate reader was established for each test to arrive at a calibration function. FIGS. 8A-8D show these calibration curves obtained for each IgG assay, which follow a logarithmic fitting that is based on the Beer's law. Each calibration curve maps the HDR normalized result obtained from the mobile phone system (i.e., C) to the optical density value at 650 nm given by gold standard clinical reader. For each type of test approximately half of the measurements were used for calibration and the other half for blind validation. On the top of each graph the number of samples (N) used to build each calibration curve is also stated: 130 samples were used for mumps IgG, 133 samples were used for measles IgG, 154 samples were used for HSV-I IgG and 150 samples were used for HSV-II IgG. Also note that the dynamic range for each IgG ELISA test is different: HSV-I IgG and HSV-II IgG cover a wide OD range between 0 and 4, while mumps and measles cover 0 to 3 and 0 to 2 ranges, respectively.

Machine Learning Algorithm

With reference to FIG. 6, in the machine learning approach, a custom designed algorithm automatically detects each well center on the image, and calculates the average, standard deviation, maximum, minimum, max-min difference of the blue channel intensities to be used as training features. In addition, as shown in FIG. 2, each test consisted of three mobile phone pictures at different exposure times ($\tau_D$, $\tau_M$, $\tau_B$); so this feature extraction was repeated over these three images separately, including the resultant HDR value of each well used as additional features. Moreover, this process was repeated using three different circular mask dimensions (with 10, 15 and 25 pixel radius) over each well center. Finally, the mobile phone clinical values (C) were also included in the feature pool, providing a total of fifty-eight (58) spatial features for characterization of each well. The fifty-eight (58) features are found looking at the following formula:

((5 Test Parameters+1 Control HDR)×3 images ($\tau_D$, $\tau_M$, $\tau_B$)+final test HDR Value)×3 mask radii+Mobile phone Reading (C) value=58 spatial features. The five (5) test parameters are: average intensity, maximum intensity, minimum intensity, difference, standard deviation of blue channel intensity of each well. A feature vector is thus created for each well with each well having fifty-eight (58) features. Gold standard labels (e.g., positive, negative, equivocal) which are provided either by a trained clinician or other expert can then be added to as part of the machine learning training program.

As seen in FIG. 6, the original RAW images from a training set of data 200 is subject to feature extraction in operation 210 whereby the fifty-eight (58) features described above are extracted from the training set of data 200. A clinical label is then applied to this extracted data as seen in operation 220. Here, since the clinical diagnosis is known in advance (e.g., positive, negative, equivocal), the extracted data is given a label to create labeled training data as seen in operation 230. A feature vector (including label) is thus created for each well of the training data. The labeled training data from operation 230 is then used to train or create a machine learning classifier 240. The machine learning classifier 240 is based on the extracted features and associated labels provided by the gold standard. The machine learning classifier 240 establishes statistical relations between the spatial features of the training data set and gold standard diagnostic labels (e.g., negative, equivocal, or positive). As explained below, these statistical relationships are then applied to the features of the test data to make blind diagnostic decisions. As seen in FIG. 6, putative test data 250 in the form of original RAW images is subject to the same feature extraction operation 210. This creates a feature vector for each well 22. Each well 22 is associated with fifty-eight (58) features. The feature vector created by the feature extraction operation is then run through the machine learning classifier 240 as seen in operation 260 to determine the proper label or well diagnosis. Each well is classified as positive (P), negative (N), or equivocal (E) as seen in operation 270.

Comparison of Diagnostic Decisions and Statistical Analysis

In order to compare the diagnostic performance of the mobile phone based, micro-plate reader, ten random trials were analyzed by splitting the available clinical measurement data in half for each disease. In other words, for each trial, half of the available data set was allocated towards training and the other half towards blind testing. This data splitting was carried out using a cross-validation technique that provides optimized training sets. Due to the statistical nature of this cross-validation method, each trial has a different and randomly selected training set. Finally, logarithmic calibration curve equations and R-Squared values reported in FIGS. 8A-8D were calculated using Microsoft Excel curve fitting tools.

Figure 9:
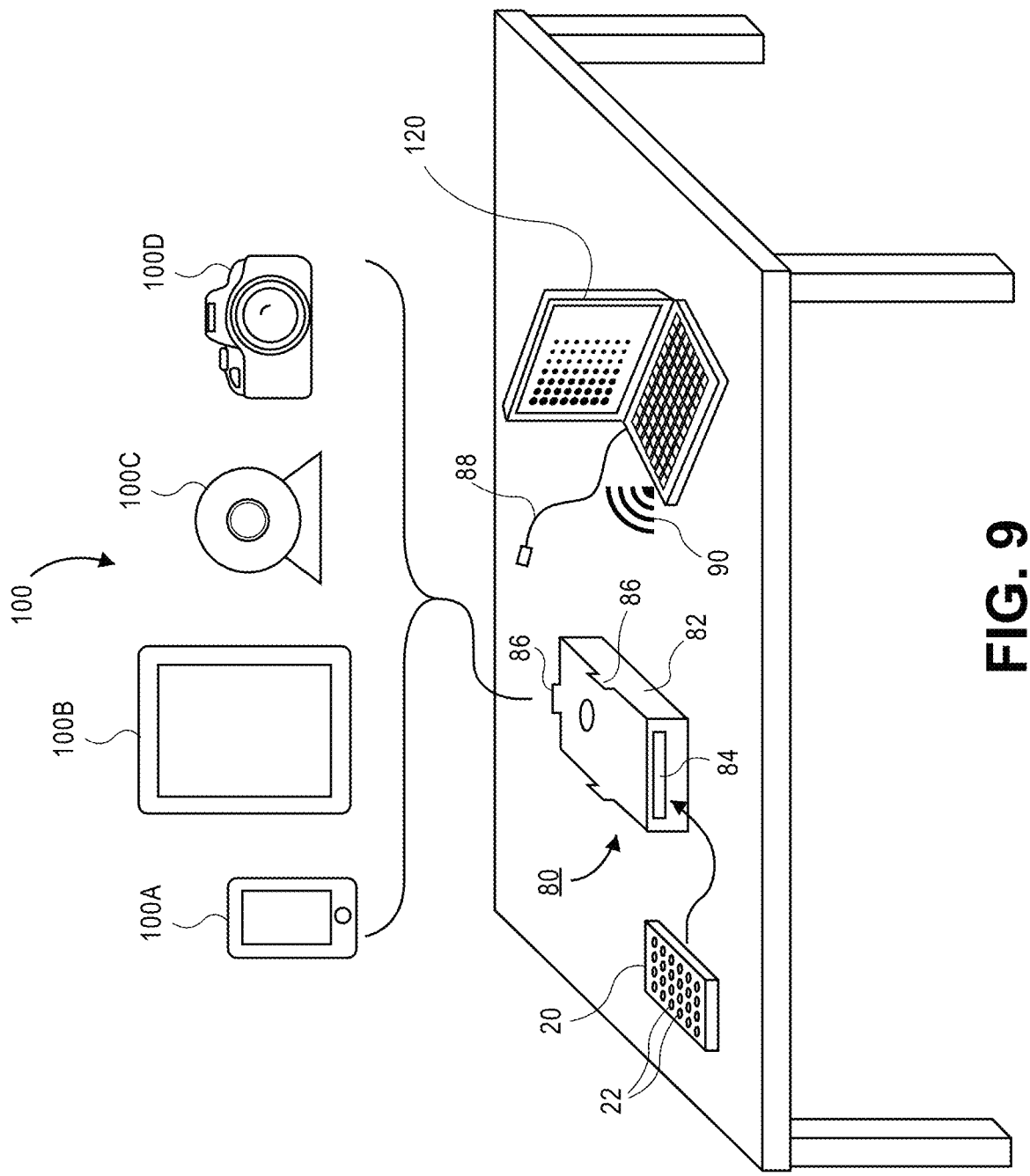
FIG. 9 illustrates an alternative embodiment of the microplate reader. This embodiment illustrates a desk or bench-top version of the device.

FIG. 9 illustrates an alternative embodiment of the micro-plate reader 80. This embodiment illustrates a desk or bench-top version of the device. Thus, the micro-plate reader 80 dues not necessarily need to be hand-held or even portable (although it may also be hand-held and portable). The micro-plate reader 80 illustrated in FIG. 9 includes an opto-mechanical attachment 82 that is similar to construction and operation of the opto-mechanical attachment 12 described herein (e.g., it includes illumination sources 16, optical fibers 24, header 26, base plate 25, power source 30, diffusion layers 32, etc.). The opto-mechanical attachment 82 includes a slot 84 that is dimensioned to receive the optically transparent plate 20 (e.g., 96-well plate) that contains the array of wells 22 therein as described previously. The opto-mechanical attachment 82 includes fasteners 86 that are used to secure a portable electronic device 100 thereto.

FIG. 9 illustrates a variety of different portable electronic devices 100 that can be secured to the opto-mechanical attachment 82 including a mobile phone 100A, tablet PC 100B, webcam 100C, and digital camera 100D. The various portable electronic devices 100A-100D are secured to the opto-mechanical attachment 82 via the fasteners 84 so as to place the camera element of the respective portable electronic device 100A-100D within an optical path of the output array of optical fibers 24 from the header 26 (not illustrated in FIG. 9). In one embodiment, the various portable electronic devices 100A-100D may connect to a separate computer 120 such as a laptop or desktop PC so that image files obtained using camera element of the portable electronic devices 100A-100D may be transferred thereto. The image files are then processed using software contained in the computer 120 to generate qualitative clinical determinations and/or quantitative index values for samples contained in the separate wells of the optically transparent plate 20 as described herein. Image files may be transferred using a cable 88 (e.g., USB cable or the like) or the files may be transmitted wirelessly using wireless communication 90. In an alternative embodiment, the portable electronic device 100A-100D may be used to digitally process images and generate the qualitative clinical determinations and/or quantitative index values. In such an embodiment, there may be no need for the separate computer 120.

While embodiments of the present invention have been shown and described, various modifications may be made without departing from the scope of the present invention. For example, different color light sources may be used. Different colors may be extracted as well. In addition, the well plate may have more than 96 wells or less than 96 wells. While 96-well plates are commonly used, other formats could also be used. Further, while the invention was described with software being used on a Windows based platform, the invention may be used on other operating systems (e.g., Android or iOS). In addition, as explained herein, image processing and well analysis (either qualitative or quantitative) may take place on the portable electronic device 100 rather than being offloaded to a remote computer 108 such as a server or a local computer 120. In addition, while the portable electronic device 100 needs to be secured to the opto-mechanical attachment 12 so that the header 26 is able to transmit light to the camera 102 one could separate the remaining portion of the opto-mechanical attachment 12 containing the optically transparent plate 20 and illumination sources 16 with a cable (containing optical fibers 24) connecting the two components. The invention, therefore, should not be limited, except to the following claims, and their equivalents.

What is claimed is:

1. A micro-plate reader for use with a mobile phone or tablet computer having a camera therein comprising:
   an opto-mechanical attachment having an upper part and a lower part that collectively define a housing and configured to attach/detach to the portable electronic device via one or more fasteners;
   an array of illumination sources disposed in the upper part of the opto-mechanical attachment;
   a slot disposed in the upper part of the opto-mechanical attachment and dimensioned to receive an optically transparent plate containing an array of wells therein, the array of wells being illuminated by the array of illumination sources when turned on;
   a plurality of optical fibers contained in the lower part of the opto-mechanical attachment, wherein each optical fiber of the plurality of optical fibers terminates at a first end in a base plate contained in the opto-mechanical attachment and forming a bottom surface of the slot to form an input array of optical fibers and terminates at a second end in a header to form an output array of optical fibers therein, wherein the output array of optical fibers in the header has a cross-sectional area that is at least 10× less than a cross-sectional area of the array of wells in the optically transparent plate; and
   a lens disposed in the upper part of the opto-mechanical attachment and interposed in an optical path formed between the array of optical fibers in the header and the camera of the mobile phone or tablet computer.

2. The micro-plate reader of claim 1, further comprising an optically transparent plate disposed in the slot, wherein the base plate comprises an array of apertures that receive the first ends of the plurality of optical fibers and wherein the array of wells aligns with the input array of optical fibers such that each well is associated with one or more optical fibers.

3. The micro-plate reader of claim 2, wherein each illumination source of the array is centered about four (4) wells.

4. The micro-plate reader of claim 2, further comprising a remote computer or a local computer executing software configured to process images taken with the camera of the mobile phone or tablet computer, wherein the software receives images of the wells of the optically transparent plate captured at a plurality of different exposure times in response to illumination by the array of illumination sources and detects each well and extracts pixel intensity of each well, wherein the application generates an intensity image/map of the wells which is normalized to create a scaled intensity/map of the wells.

5. The micro-plate reader of claim 4, the software further configured to covert the scaled intensity/map of the wells to clinical index values in response to a calibration curve or conversion factor.

6. The micro-plate reader of claim 5, the software is further configured to generate a qualitative clinical determination based on a thresholding of the clinical index values.

7. The micro-plate reader of claim 1, further comprising at least one diffuser interposed between the array of illumination sources and the optically transparent plate.

8. The micro-plate reader of claim 1, wherein the the mobile phone or tablet computer contains an application thereon configured to process images taken with the camera of the mobile phone or tablet computer, wherein the application receives images of the wells of the optically transparent plate captured at a plurality of different exposure times in response to illumination by the array of illumination sources and detects each well and extracts pixel intensity of each well, wherein the application generates an intensity image/map of the wells which is normalized to create a scaled intensity/map of the wells and converted to clinical index values in response to a calibration curve or conversion factor and displayed for each well of the array.

9. The micro-plate reader of claim 8, wherein the application is further configured to generate a clinical determination based on a thresholding of the clinical index values.

10. The micro-plate reader of claim 1, wherein the array of illumination sources comprise a plurality of light emitting diodes (LEDs) or a plurality of laser diodes.

* * * * *